(12) United States Patent
Ueda et al.

(10) Patent No.: US 8,251,885 B2
(45) Date of Patent: Aug. 28, 2012

(54) APPLICATIONS OF ALTERNATING MAGNETIC FIELDS ON MAGNETIC NANOPARTICLES

(75) Inventors: Tomoaki Ueda, Kyoto (JP); Masanori Abe, Tokyo (JP); Hiroshi Handa, Tokyo (JP)

(73) Assignee: Empire Technology Development LLC, Wilmington, DE (US)

( * ) Notice: Subject to any disclaimer, the term of this patent is extended or adjusted under 35 U.S.C. 154(b) by 409 days.

(21) Appl. No.: 12/564,695

(22) Filed: Sep. 22, 2009

(65) Prior Publication Data
US 2011/0071335 A1    Mar. 24, 2011

(51) Int. Cl.
*A61M 37/00* (2006.01)
*A61N 2/00* (2006.01)

(52) U.S. Cl. ............................................. 600/12; 600/9
(58) Field of Classification Search ..................... 600/12, 600/9
See application file for complete search history.

(56) References Cited

U.S. PATENT DOCUMENTS

| 7,548,787 | B2 | 6/2009 | Feher | |
| 7,741,840 | B1* | 6/2010 | Sandhu | 324/214 |
| 2003/0078493 | A1* | 4/2003 | Ogawa et al. | 600/420 |
| 2003/0105382 | A1* | 6/2003 | Brown et al. | 600/12 |
| 2006/0142630 | A1 | 6/2006 | Meretei | |
| 2007/0010702 | A1 | 1/2007 | Wang et al. | |
| 2007/0244388 | A1* | 10/2007 | Sato et al. | 600/424 |
| 2009/0209900 | A1* | 8/2009 | Carmeli et al. | 604/22 |

FOREIGN PATENT DOCUMENTS

WO   WO 2009074952 A2 *   5/2009
WO   PCT/US2010/036604     2/2011

OTHER PUBLICATIONS

Forgacs, R. L.; Warnick, A.; , "Digital—Analog Magnetometer Utilizing Superconducting Sensor," Review of Scientific Instruments , vol. 38, No. 2, pp. 214-220, Feb. 1967.*
National Instruments Tutorial/Whitepaper, "Understanding Direct Digital Synthesizer (DDS)" Sep. 5, 2008.*

* cited by examiner

*Primary Examiner* — Charles A Marmor, II
*Assistant Examiner* — Sunita Reddy
(74) *Attorney, Agent, or Firm* — Workman Nydegger

(57) ABSTRACT

Embodiments include applying or generating an alternating magnetic field near an affected area of a subject to be treated. When magnetic nanoparticles are located in the affected area, the magnetic nanoparticles are oscillated by the alternating magnetic field, which causes the magnetic nanoparticles to be dispersed within the affected area, break up the affected area, and/or heat the affected area.

18 Claims, 10 Drawing Sheets

APPLICATIONS OF ALTERNATING MAGNETIC FIELDS ON MAGNETIC NANOPARTICLES

TECHNICAL FIELD

Embodiments described herein can broadly be used in technical fields implicating nanotechnology. Some embodiments include applying nanotechnology to perform medical applications.

BACKGROUND

Magnetic nanoparticles have been used in medical fields such as MRIs, drug delivery systems, and magnetic hyperthermia. Magnetic nanoparticles are also used in thrombus treatment to break/destroy thrombus plaque in blood vessels and are activated using a strong magnetic field, such as one generated by an MRI. However, MRIs are expensive devices and the magnetic field generated by an MRI can cause the magnetic nanoparticles to damage the healthy tissue.

DETAILED DESCRIPTION

Figure 1A:
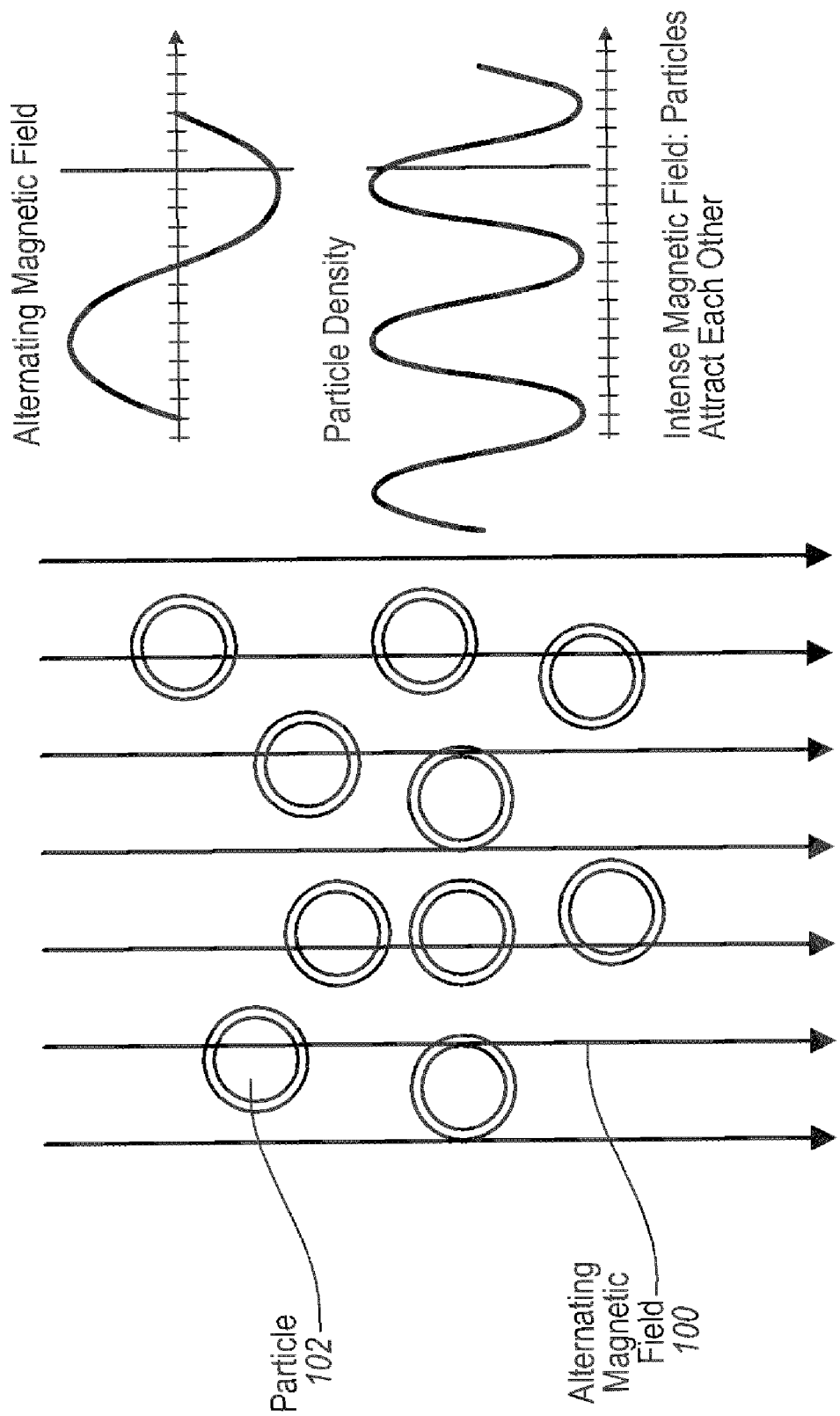
FIG. 1A illustrates a principal of interaction between magnetic nanoparticles with an alternating magnetic field when the magnetic field is generated strongly.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Magnetic nanoparticles have been used in medical fields to break and destroy various biomediums, such as thrombus plaque in blood vessels. However, this has typically required expensive equipment to provide strong magnetic fields with enough energy to move the magnetic nanoparticles. The large amounts of electrical current can create unwanted heat. In addition, magnetic coils have typically been required to be large such that a subject is placed within the magnetic coil. Conventional methods have thus posed potential damage to healthy tissue in which magnetic nanoparticles are placed.

The present disclosure provides methods, apparatuses, systems, computer programs, and other embodiments for using magnetic nanoparticles in a manner that is safe to biosystems for at least partially disrupting, break up, agitate, mix, excite and/or heat an affected area. Aspects of the disclosure apply an alternating current to a magnetizing coil to excite an alternating magnetic field of the magnetizing coil. When the alternating magnetic field is applied near one or more magnetic nanoparticles, the alternating magnetic field is effective to increase an oscillation of the one or more magnetic nanoparticles. As used herein, the term "near" broadly covers any distance sufficient for the alternating magnetic field to effect and/or affect the oscillation of the one or more magnetic nanoparticles. In one embodiment, "near" can include that the magnetizing coil being located "at" or very near to the location holding the magnetic nanoparticles. The distance at which the alternating magnetic field is applied may also depend on the intensity of the alternating magnetic field. For example, an alternating magnetic field having a stronger intensity may be located farther away from the location holding the magnetic nanoparticles than an alternating magnetic field having a lower intensity.

Thus, some embodiments are directed to magnetic nanoparticles that are placed in a medium at a predetermined location and caused to oscillate using an alternating current to disperse and treat an affected area at the predetermined location. An example of a medium at a predetermined location is a thrombus in a blood vessel. Embodiments include applying or generating an alternating magnetic field near an affected area of a subject to be treated. When magnetic nanoparticles are located in the affected area, the magnetic nanoparticles are oscillated by the alternating magnetic field, which causes the magnetic nanoparticles to be dispersed within the affected area, break up the affected area, and/or heat the affected area.

As used herein, the term "affected area" broadly refers to a predetermined location where a treatment utilizing magnetic nanoparticles will be applied. An affected area can be identified by diagnosis by a medical professional during a physical exam, an MRI, a CAT scan, or any of a variety of medical analysis which can detect areas in which the treatments herein may be beneficial. Treatment can include any process in which it is desired to influence an affected area by moving magnetic nanoparticles within the affected area so as to be dispersed within the affected area. The movement of the magnetic nanoparticles within the affected area can cause additional beneficial effects to occur, such as, but not limited to, the affected area being disrupted, broken up, agitated, mixed, heated, excited, and the like. In some embodiments, the affected area may include a medium in which the magnetic nanoparticles are placed. When the subject is a human body, the medium may be a thrombus, biofluids, tissue, blood vessels, and the like. A used herein, the term "medium" refers to a substance in which the magnetic nanoparticles are placed that is able to become excited by the oscillation of the magnetic nanoparticles and propagate acoustic signals generated by the oscillating magnetic nanoparticles. Thus, depending on the medium, a viscosity of the medium may affect how easily magnetic nanoparticles are able to oscillate within the medium. For example, when an affected area contains thrombus plaque, the predetermined location may be thrombus plaque located in a blood vessel having a diameter of about 1,000 nm or less with the medium being the thrombus plaque. In this example, the magnetic nanoparticles may thus be placed in a region of 1,000 nm or less. In another embodiment, the magnetic nanoparticles may be placed in a larger region.

As used herein, the term "magnetic nanoparticles" broadly covers particles having ferromagnetic, ferrimagnetic, paramagnetic and superparamagnetic properties. The magnetic nanoparticles may be synthesized from various materials, such as, but not limited to, ferrite, ferrite alloy, nickel, platinum, and the like. In addition, mixtures of ferrite with non-metal material (such as silica and polymer) may be used to synthesize the magnetic nanoparticles, thus providing the desired magnetic properties in the presence of what are traditionally non-magnetic compounds (e.g., silica and polymer).

In an illustrative embodiment, magnetic nanoparticles are a superparamagnetic parenteral iron oxide contrast agent sold under the trademark Resovist® and manufactured by Shering AG. In an illustrative embodiment, magnetic nanoparticles are ferumoxides sold under the trademark Feridex® and manufactured by Amag Pharmaceuticals.

Depending on the medium of the affected area and the composition of the magnetic nanoparticles that may be placed in the affected area for treatment, ferromagnetic or ferrimagnetic magnetic nanoparticles tend to aggregate due to remanent magnetization when no alternating current is being applied, making it more difficult to disperse the magnetic nanoparticles within the affected area when the alternating current is actually applied. In one embodiment, the magnetic nanoparticles can be composed of superparamagnetic material which is able to be strongly magnetized with little or no remanent magnetization to prevent the magnetic nanoparticles from aggregating when placed within a medium at the affected area.

In one embodiment, the magnetic nanoparticles can be placed in the medium as individual particles. In another embodiment, the magnetic nanoparticles can be placed in the medium as a cluster of particles that operate as a working unit. For example, if the magnetic nanoparticles is made of pure metal, it may be desirable to use magnetic nanoparticle having a diameter of less than 10 nm due to issues of remanent magnetization and safety. However, as discussed further below, an acoustic signal can, in some situations, be generated more easily where a diameter of an acting particle on the medium is of larger size than 10 nm. Thus, in one embodiment, a cluster of magnetic nanoparticles, such as two or three particles, can be synthesized and placed in a shell to operate as a working unit. In another embodiment, the magnetic nanoparticles may loosely aggregate after being placed in the medium. For example, in one embodiment, Resovist® magnetic particles are used that contain superparamagnetic iron oxide coated with Carboxi dextran. When the Resovist® particles are administered to the affected area, the particles generally are not aggregated. Then, when a magnetic field is applied to the Resovist® particles, the particles begin to oscillate and at least some of the particles become loosely aggregated. The individual particles and the loosely aggregated clusters each operate as "working units". The working unit then has the benefit of larger size, while maintaining the individual magnetic nanoparticles at smaller sizes. Given the variation of types of magnetic nanoparticles and possible clustering configurations that can be used, it is helpful to reference an "acting particle" diameter that refers to a diameter of a particle that is actually placed in the medium. The "acting particle" can be an individual nanoparticle. Or, alternatively, the "acting particle" can be a cluster of nanoparticles operate together as a working unit, whether combined together in a shell, or loosely aggregated together.

The shape of the acting particle can be configured to be any shape such as, but not limited to, spherical, elliptical, cylindrical, cubical, conical, pyramidal, tetrahedral, and the like. In some embodiments, a diameter of each of the acting particle can depend on the size of the affected area in which the acting particle is to be applied. However, those skilled in the art will recognize that the acting particle can be synthesized to whatever suitable size is needed for a particular treatment. Further, one or more acting particles may be placed in a particular location. As also discussed below, the diameter of the acting particle can also be affected by including a resistance-generating structure or resistance-decreasing structure. A suitable diameter for an acting particle can thus range from about 3 nm to about 100 nm, or from about 10 nm to about 100 nm, or from about 15 nm to about 30 nm, or from about 15 nm to about 25 nm, as illustrative examples. The remainder of this disclosure may use the term "magnetic nanoparticle" as synonymous and interchangeable with the term "acting particle." The size of the acting particle is generally determined by the size of the affected area and the purpose for which the acting particles are being used. For example, where the affected area is a blood vessel with a diameter of about 1,000 nm or less that has thrombus plaque, the acting particles must be small enough to allow fluid flow in the blood vessel. When the thrombus is broken up, at least some of the acting particles could be flushed downstream to smaller veins. Thus, in this example, the size of the magnetic nanoparticles in selected so that magnetic nanoparticles will not block blood flow in the blood vessel and/or other veins. However, where magnetic nanoparticles blocking fluid flow is not a potential concern, then the size of the magnetic nanoparticles can be larger, and, in some instances, will actually have better oscillation properties due to having a larger size. Thus, the example sizes provided above are for illustrative purposes only and are not limiting.

When the magnetic nanoparticles are oscillated by the magnetic field, an acoustic signal is generated in the medium by the magnetic nanoparticles and the magnetic nanoparticles transfer the momentum to the medium. When a resistance of a magnetic nanoparticle toward the medium is small, a large acoustic signal cannot be generated by the magnetic nanoparticle even though the magnetic nanoparticle is oscillating quite strongly. In other words, in order to move the surrounding medium to create the large acoustic signal (with large amplitude), the magnetic nanoparticles must be able to move the medium. In some cases, the medium cannot be moved even where the magnetic nanoparticles are rapidly moving or oscillating. Based on Stokes' theorem, when a particle with small diameter has small frictional force with molecules of the surrounding medium, the small particle cannot generate a large acoustic wave (even though the small particle may be oscillating very fast), leaving the molecules of the surrounding medium essentially immobile. Therefore, in order to create a large acoustic wave, the frictional force between the magnetic nanoparticles and the surrounding medium needs to be large. Further, since it will be the surrounding medium that transmits the acoustic wave so that it is detectable by a detecting device (see below), the surrounding medium needs to be oscillated along with the magnetic nanoparticles.

To overcome the situation where a magnetic nanoparticle does not have enough resistance to be able to generate an acoustic wave in a medium, a larger diameter magnetic nanoparticle can be selected for use since the greater the diameter of the magnetic nanoparticles, the greater the frictional force will be. In another embodiment, instead of increasing the size of the magnetic nanoparticles, a coating can be applied to a surface of the magnetic nanoparticles, the coating having a resistance generating structure that generates a larger frictional force with the surrounding medium than the magnetic nanoparticle does by itself. In one embodiment, the resistance generating structure creates a resistance up to ten times greater than a resistance of a magnetic nanoparticle that does not have the resistance generating structure. The resistance generating structure may be selected from, but is not limited to, sugar, gel matrix, styrene polymer, and the like, or a combination thereof. In one embodiment, the resistance generating structure provides a steric structure of at least a portion of the magnetic nanoparticle to be more three-dimensional, so that when the magnetic nanoparticle with the resistance generating structure having the more three-dimensional steric structure is placed in the medium, the magnetic nanoparticle generates a larger frictional force between the magnetic nanoparticles and the medium.

A determination that a resistance between the magnetic nanoparticle and the medium is too low can be made before the magnetic nanoparticles are placed in the medium, as described in more detail below. A determination can be made whether sufficient resistance will exist between the magnetic nanoparticle and the medium to generate the desired acoustic signal, depending on a variety of factors such as terminal velocity (speed) and particle diameter. Resistance can also depend on how particles aggregate and operate together as working units, as described below in further detail.

Thus, when the resistance is below the range or threshold of resistance, measures can be taken to increase the resistance, such as, but not limited to, selecting magnetic nanoparticles of larger size, or placing a resistance-increasing coating on the magnetic nanoparticles to increase resistance. In one embodiment, the resistance-increasing coating can provide a particular steric structure that is more three-dimensional.

On the other hand, when the resistance of the magnetic nanoparticle toward the medium is too large, there is too much resistance between the magnetic nanoparticle and the medium so that a large acoustic signal also cannot be generated. That is, when the frictional force between the magnetic nanoparticles and the surrounding medium is too large, a driving energy caused by the magnetic field turns oscillations of the magnetic nanoparticle to heat energy immediately without generating an acoustic wave. In these situations, even when the magnetic nanoparticles are moved by a magnetic field or when the magnetic nanoparticles generate heat, the amount of the momentum of the magnetic nanoparticles and heat generated by the momentum is not sufficient to break up the affected area. Thus, the selection of the appropriate frictional force (or acoustic impedance matching) can generate the desired acoustic wave.

To overcome the situation where a magnetic nanoparticle has too much resistance with the medium such that it produces heat instead of the desired acoustic wave, a magnetic nanoparticle of a smaller diameter can be selected for use in the medium. In other embodiments, a resistance-decreasing structure can be applied to a surface of the magnetic nanoparticles to decrease the resistance between the magnetic nanoparticles and the surrounding medium. For example, when the medium is water, the resistance decreasing structure may be selected from, but not limited to, water-shedding material, or lipophilic material, or a combination thereof. In one embodiment, the resistance decreasing structure provides a steric structure of the magnetic nanoparticles to be less three-dimensional to decrease the amount of resistance between the magnetic nanoparticle and the surrounding medium.

A determination that a resistance between the magnetic nanoparticle and the medium is too high can be made before the magnetic nanoparticles are placed in the medium. For example, using the calculations provided above, knowing the speed of the particle, the size of the particle, and the viscosity of the medium, a determination can be made whether sufficient resistance will exist between the magnetic nanoparticle and the medium to generate the desired acoustic signal. Thus, when the resistance is above the range or threshold of resistance, measures can be taken to decrease the resistance, such as, but not limited to, selecting magnetic nanoparticles of smaller size, or placing a resistance-decreasing coating on the magnetic nanoparticles to decrease resistance. In one embodiment, the resistance-decreasing coating can have a particular steric structure that is less three-dimensional.

Thus, one aspect of the invention includes a method for a medical treatment, the method including applying an alternating magnetic field near one or more magnetic nanoparticles at a first location. The application of the alternating magnetic field is effective for increasing an oscillation of the one or more magnetic nanoparticles at the first location. The alternating magnetic field can be maintained to oscillate one or more magnetic nanoparticles. The method can include applying an alternating current to a magnetizing coil to excite the alternating magnetic field of the magnetizing coil. The method can include measuring the alternating magnetic field generated by the magnetizing coil and an acoustic signal generated by the magnetic nanoparticles. The method can include comparing the measurement of the alternating magnetic field and the measurement of the acoustic signal to detect a doubled acoustic frequency. The method can include generating an output based on the comparison.

Another aspect of the invention is an apparatus having a magnetizing coil, a current driver amplifier coupled to the magnetizing coil, and a direct digital synthesizer connected to the current driver amplifier, that when in operation, operates with the current driver amplifier to supply an alternating current to the magnetizing coil to generate an alternating magnetic field in the magnetizing coil. The apparatus can further include an acoustic probe, a preamplifier connected to the acoustic probe, that when in operation, operates with the preamplifier and acoustic probe to measure an acoustic signal generated by the alternating magnetic field, and a double frequency synchronous cross-detector connected to the preamplifier and connected to the direct digital synthesizer, the direct digital synthesizer configured to measure the alternating magnetic field generated in the magnetizing coil. The double frequency synchronous cross detector compares the measurement of the acoustic signal and the measurement of the alternating magnetic field and generates a doubled acoustic frequency.

Another aspect is a system for a medical treatment including a magnetizing coil configured to be placed near a first location having a plurality of magnetic nanoparticle, an alternating current generator coupled to the magnetizing coil to generate an alternating magnetic field in the magnetizing coil, an acoustic probe configured to be placed near the first location having the plurality of magnetic nanoparticles, a first detector communicating with the alternating current generator for generating a first measurement of an alternating magnetic field generated in the magnetizing coil, and a second detector communicating with the acoustic probe for generating a second measurement of an acoustic signal generated by the plurality of nanoparticles oscillating at the first location by the magnetic field.

The system optionally further includes a computing device communicating with the first detector and the second detector, the computing device having a processor and memory, the memory comprising one or more instructions that when executed by the processor cause the computing device to receive the first measurement of the alternating magnetic field generated in the magnetizing coil, receive the second measurement of the acoustic signal generated by the plurality of nanoparticles oscillating at the first location by the magnetic field, and compare the measurement of the alternating magnetic field and the measurement of the acoustic signal to detect a doubled acoustic frequency. The processor can also generate an output based on the comparison. And, a graphical user interface can communicate with the processor to graphically display the output.

Aspects also include computer program products for use in a computer system having a processor and storage, the computer product comprising a signal-bearing medium having computer executable instructions that, when executed by the processor of the computer system cause the computer system to perform a method for activating one or more magnetic nanoparticles at a predetermined location in a medium, the method comprising applying an alternating magnetic field near one or more magnetic nanoparticles at a first location. The application of the alternating magnetic field is effective for increasing an oscillation of the one or more magnetic nanoparticles at the first location. The alternating magnetic field can be maintained to oscillate one or more magnetic nanoparticles. The method can include applying an alternating current to a magnetizing coil to excite the alternating magnetic field of the magnetizing coil. The method can include measuring the alternating magnetic field generated by the magnetizing coil and an acoustic signal generated by the magnetic nanoparticles. The method can include comparing the measurement of the alternating magnetic field and the measurement of the acoustic signal to detect a doubled acoustic frequency. The method can include generating an output based on the comparison.

FIG. 1A illustrates a principal of interaction between magnetic nanoparticles with an alternating magnetic field when the alternating magnetic field is generated having a magnetic induction of about 0.5 mT and above. When a strong alternating magnetic field (e.g., magnetic induction of over 0.5 mT) indicated by lines 100 is applied to magnetic nanoparticles 102, the strong alternating magnetic field causes the magnetic nanoparticles to experience acceleration, and, thus, motion. As discussed below, the alternating magnetic field causes the magnetic nanoparticles to move in both the transverse and longitudinal directions.

Figure 1B:
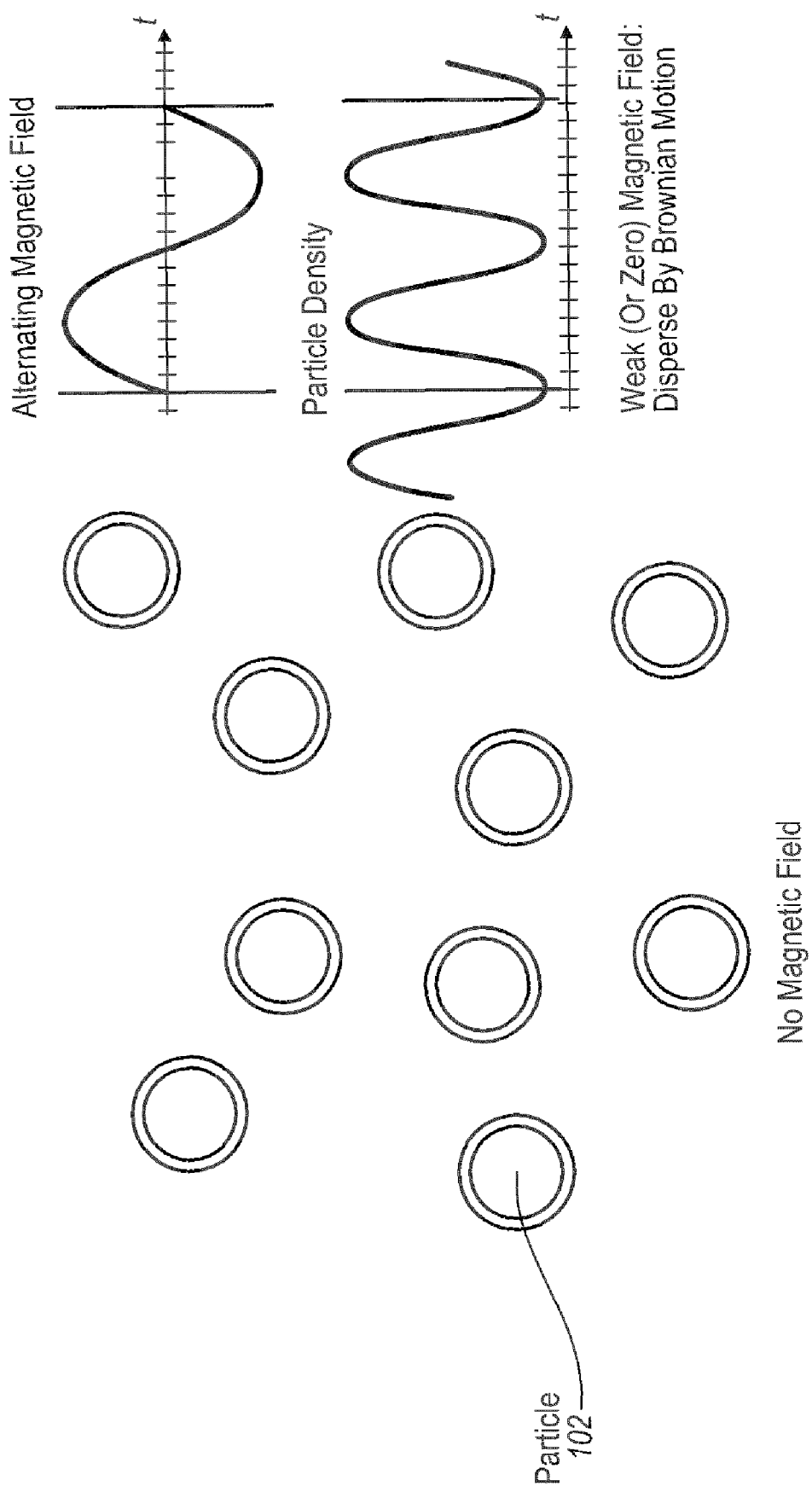
FIG. 1B illustrates a principal of interaction between magnetic nanoparticles with an alternating magnetic field when the magnetic field is 0 (zero) or weak intensity.

FIG. 1B illustrates a principal of interaction between magnetic nanoparticles with an alternating magnetic field when the alternating magnetic field is 0 (zero) or weak intensity. A zero or weak intensity is where the magnetic induction is 0 to 0.5 mT. When there is no or a weak magnetic field, the magnetic nanoparticles 102 are dispersed by Brownian relaxation.

Principles of operation of an alternating magnetic field being applied to magnetic nanoparticles will now be described. A magnetic force, F, generated by magnetization is calculated by the following equation:

$$F = \mu_0 \chi_m H \frac{\partial H}{\partial x}$$

where $\mu_0$ indicates space permeability, $X_m$ indicates a mass magnetic susceptibility, H indicates the strength of the magnetic field, and x indicates a coordinate position in x-axis direction. Thus, $\partial H/\partial x$ indicates a local magnetic gradient. For instance, the local magnetic gradient of an apparatus such as an MRI is small. If a large gradient can be created, it is possible to create a large force with small H (magnetic field intensity).

When magnetic nanoparticles are present in a medium, a magnetic force works on the magnetic nanoparticles in a non-homogeneous magnetic field. At the same time, the reversed force works on the medium itself. As such, both the magnetic nanoparticles and the medium experience a magnetic force due to the magnetic field. Then, the force working on the magnetic nanoparticles in a medium is indicated by the equation:

$$F = \mu_0 (\chi_p - \chi_f) V H \frac{\partial H}{\partial x}$$

where $X_p$ is a volume magnetic susceptibility of the magnetic nanoparticles, $X_f$ is a volume magnetic susceptibility of the medium, and V indicates volume of the site.

In this case, when the magnetic nanoparticles are oscillated by the magnetic force, F, the magnetic nanoparticles experience an increase in acceleration to some extent. When a speed of the momentum of the magnetic nanoparticles reaches a speed that counterbalances with a viscosity resistance of the medium, then the speed of the magnetic nanoparticle cannot exceed a terminal speed given by the following equation:

$$v = \frac{2\mu_0 (\chi_p - \chi_f) r^2}{9\eta} H \frac{\partial H}{\partial x}$$

where v indicates the speed of the magnetic nanoparticles, $\eta$ indicates a viscosity of a medium, and r indicates a radius of the magnetic nanoparticle.

Figure 2:
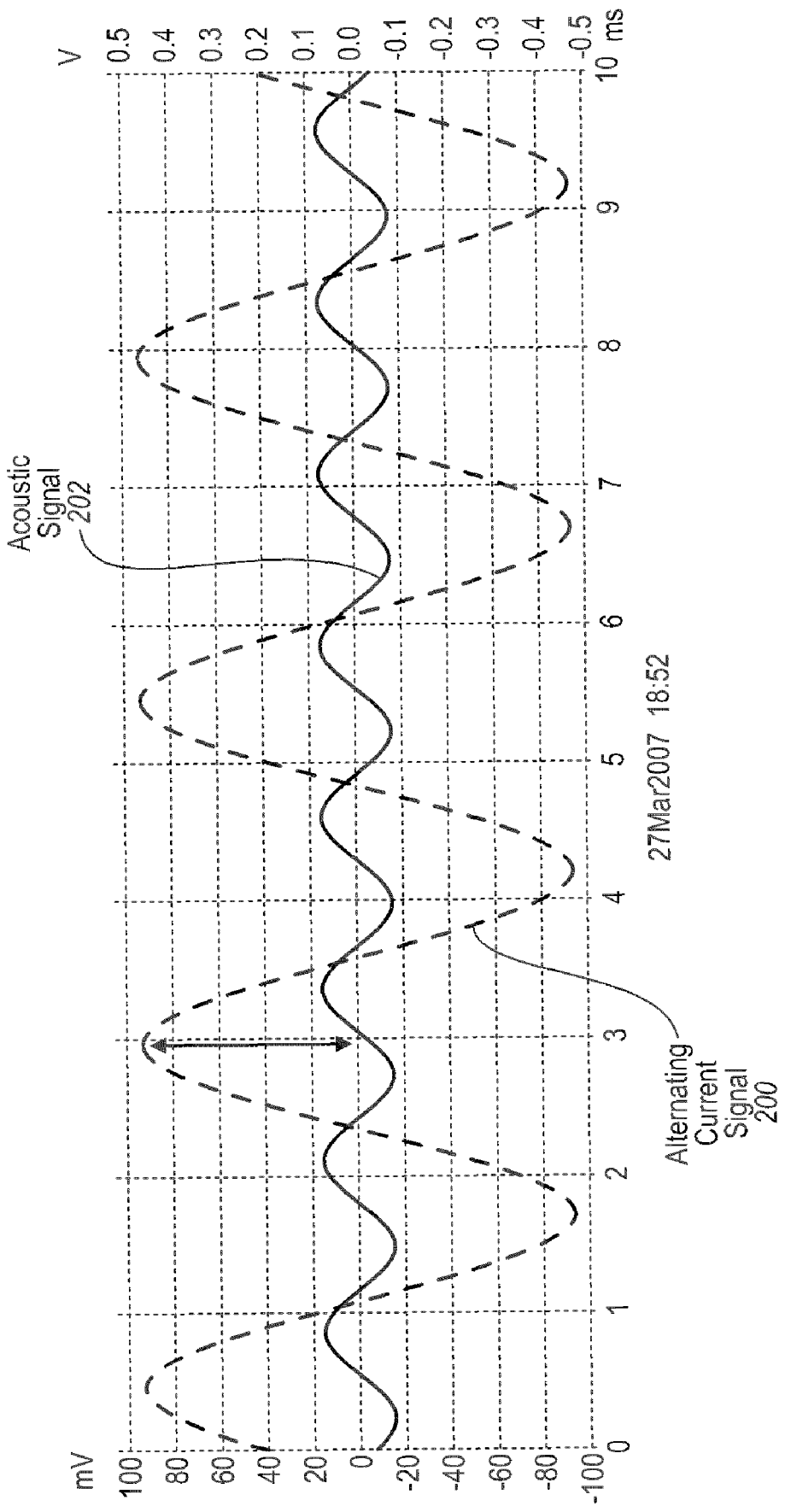
FIG. 2 is a graph showing an illustrative embodiment of a correlation between an excited alternating current signal and an acoustic signal generated by the magnetic nanoparticles.

When the magnetic nanoparticles are oscillated by the magnetic field, an acoustic signal is generated in the medium by the magnetic nanoparticles and the magnetic nanoparticles transfer the momentum to the medium. FIG. 2 is a graph showing a correlation between an alternating current signal 200 (shown as a dashed line) and an elastic wave or acoustic signal 202 (shown in a solid line) generated by the magnetic nanoparticles when an alternating magnetic field is applied to the magnetic nanoparticles.

When a resistance of a magnetic nanoparticle toward the medium is small, a large acoustic signal cannot be generated by the magnetic nanoparticle even though the magnetic nanoparticle is oscillating quite strongly. In other words, in order to move the surrounding medium to create the large acoustic signal (with large amplitude), the magnetic nanoparticles must be able to move the medium. In some cases, the medium cannot be moved even where the magnetic nanoparticles are rapidly moving or oscillating. Based on Stokes' theorem, when a particle with small diameter has small frictional force with molecules of the surrounding medium, the small particle cannot generate a large acoustic wave (even though the small particle may be oscillating very fast), leaving the molecules of the surrounding medium essentially immobile. Therefore, in order to create a large acoustic wave, the frictional force between the magnetic nanoparticles and the surrounding medium needs to be large. Further, since it will be the surrounding medium that transmits the acoustic wave so that it is detectable by a detecting device (see below), the surrounding medium needs to be oscillated along with the magnetic nanoparticles.

To overcome the situation where a magnetic nanoparticle does not have enough resistance to be able to generate an acoustic wave in a medium, a larger diameter magnetic nanoparticle can be selected for use since the greater the diameter of the magnetic nanoparticles, the greater the frictional force will be. In another embodiment, instead of increasing the size of the magnetic nanoparticles, a coating can be applied to a surface of the magnetic nanoparticles, the coating having a resistance generating structure that generates a large frictional force with the surrounding medium than the magnetic nanoparticle does by itself. In one embodiment, the resistance generating structure creates a resistance up to ten times greater than a resistance of a magnetic nanoparticle that does not have the resistance generating structure. The resistance generating structure may be selected from, but is not limited to, sugar, gel matrix, styrene polymer, and the like, or a combination thereof. In still another embodiment, the resistance generating structure provides a steric structure of at least a portion of the magnetic nanoparticle to be three-dimensional, so that when the magnetic nanoparticle having the resistance generating structure with the selected steric structure is placed in the medium, the magnetic nanoparticle generates a larger frictional force between the magnetic nanoparticles and the medium.

A determination that a resistance between the magnetic nanoparticle and the medium is too low or too high can be made before the magnetic nanoparticles are placed in the medium. For example, knowing the speed of the particle, the size of the particle, and the viscosity of the medium, a determination can be made whether sufficient resistance will exist between the magnetic nanoparticle and the medium to generate the desired acoustic signal.

Fluid resistance can generally be calculated by Stoke's law, $$F_v = 6\pi\eta r v$$

where v indicates a speed of the magnetic nanoparticles, η indicates a viscosity of a medium in which the magnetic nanoparticles are placed, and r indicates a radius of each magnetic nanoparticle. Based on the equation above of Stoke's Law, one would expect when magnetic nanoparticles of the same mass and same volume are located in a fluid, the fluid friction experienced by each magnetic nanoparticle is proportional to its radius. However, magnetic nanoparticles tend to make loosely arranged clusters that operate as working units or "acting particles" described above, where each magnetic nanoparticle in the cluster has space to move, oscillate and create energy. In this situation, there may be an overall radius $r_o$ of the acting particle and an individual radius $r_1$ of each magnetic nanoparticle in the acting particle. Since the combined volume of the magnetic nanoparticles combine to form the volume of the working unit, the resistance equation can be rewritten as:

$$F_v = 6\pi\eta r_1 \left( \frac{\frac{4\pi r_0^3}{3}}{\frac{4\pi r_1^3}{3}} \right) v = 6\pi\eta \frac{r_0^3}{r_1^2} v$$

So, as the size of the acting particle ($r_o$) increases, so does the resistance. Further, it can be noted, that as the size of the magnetic nanoparticles ($r_1$) becomes smaller, the resistance also increases. Thus one embodiment includes providing loosely aggregated acting particles made up of much smaller magnetic nanoparticles. Adding resistance generating/decreasing structures can also affect the size of the magnetic nanoparticles and/or acting particles, as described below.

The resistance depends on the viscosity of the medium and will vary depending upon the medium in which the magnetic nanoparticles are placed, a number and size of the magnetic nanoparticles, a type of fluid at the affected area, and the structure of the affected area. Further, the viscosity of the medium changes based on the structure of the affected area, e.g. the speed of blood flow near a vein wall is slower than in the middle of the vein because the viscosity changes according to the location (i.e., the viscosity near the vein wall increases).

Thus, when the resistance is below the range or threshold of resistance, measures can be taken to increase the resistance, such as, but not limited to, selecting magnetic nanoparticles of larger size, or placing a resistance-increasing coating on the magnetic nanoparticles to increase resistance. In one embodiment, the resistance-increasing coating provides magnetic nanoparticles having a particular steric structure that is more three-dimensional.

On the other hand, when the resistance of the magnetic nanoparticle toward the medium is too large, a large acoustic signal also cannot be generated. That is, a driving energy caused by the magnetic field turns to heat energy immediately without generating an acoustic wave when the frictional force between the magnetic nanoparticles and the surrounding medium is too large. In these situations where the acoustic signal is not within the desired size range, even when the magnetic nanoparticles are moved by a magnetic field or when the magnetic nanoparticles generate heat, the amount of the momentum of the magnetic nanoparticles and heat generated by the momentum is not sufficient to break up the affected area. Thus, the selection of the appropriate frictional force (or acoustic impedance matching) can generate the desired acoustic wave.

To overcome the situation where a magnetic nanoparticle has too much resistance with the medium such that it produces heat instead of the desired acoustic wave, a magnetic nanoparticle of a smaller diameter can be selected for use in the medium. In other embodiments, a resistance-decreasing structure can be applied to a surface of the magnetic nanoparticles to decrease the resistance between the magnetic nanoparticles and the surrounding medium. For example, when the medium is water, the resistance decreasing structure may be selected from, but not limited to, water-shedding material, or lipophilic material, or a combination thereof. In one embodiment, the resistance decreasing structure provides a steric structure of the magnetic nanoparticles to be less three-dimensional to decrease the amount of resistance between the magnetic nanoparticle and the surrounding medium.

Thus, when the resistance is above the range or threshold of resistance, measures can be taken to decrease the resistance, such as, but not limited to, selecting magnetic nanoparticles of smaller size, or placing a resistance-decreasing coating on the magnetic nanoparticles to decrease resistance. In one embodiment, the resistance-decreasing coating provides magnetic nanoparticles having a particular steric structure that is less three-dimensional.

The following will now discuss aspects of the alternating magnetic field. A conventional magnetic field generating device such as an MRI generates a direct magnetic field and requires a large amount of electricity to operate. Further, a direct magnetic field generally moves magnetic nanoparticles in a transverse direction, causing the magnetic nanoparticles to just move side to side, which does not break thrombus plaque efficiently. To move the magnetic nanoparticle more dynamically, a device applying a direct magnetic field would require a larger current, but this requires increased amounts of energy and the increased transverse movement of the magnetic nanoparticle can also damage healthy tissues in the process of breaking the thrombus plaque.

Embodiments herein employ an alternating magnetic field generated by an alternating current. Advantageously, an alternating current uses relatively small amounts of energy. In addition, the alternating magnetic field induces the magnetic nanoparticles to move in both transverse and longitudinal directions, which movement breaks up thrombus plaque more efficiently.

To illustrate this concept, consider where the treatment site is a blood vessel. The longitudinal axis of the blood vessel is the X axis, and the Y and Z axis are orthogonal to each other and form a plane orthogonal to the X axis. The direction of oscillation of the magnetic nanoparticles can be controlled from outside the blood vessel so that a direct current field and alternating current field operate orthogonally to each other. This focuses the direction of the magnetic flux line of the alternating current field to be along the X-axis. As can be appreciated, the magnetic nanoparticles will oscillate in the direction of the magnetic flux line (i.e., along the longitudinal axis of the blood vessel) as well as in the transverse directions Y and Z. Thus, the movement will be distributed in all three directions instead of directly against the blood vessel walls, thus reducing damage to healthy tissue. In one embodiment, the alternating current includes a direct current (DC) component and an alternating current (AC) component. Even though the magnetic nanoparticles have a greater movement, alternating excitation actually results in less damage to healthy tissue because in the example above, the particles oscillate in the direction of the magnetic flux.

When an alternating current is applied to a magnetizing coil, the alternating magnetic field is generated. This may be referred to herein as "exciting the magnetizing coil" or "exciting an alternating magnetic field," but should be understood to broadly refer to generating an alternating magnetic field. In turn, the alternating magnetic field causes magnetic nanoparticles upon which it is applied to oscillate, become activated, or become excited, all of which terms are used interchangeably.

When the magnetic nanoparticles oscillate and have sufficient resistance with the medium, an acoustic signal is generated through the medium. An acoustic signal generally suitable for biosystems can range from about 100 Pa to about 1 mPa, or from about 0.01 mPa to about 1 mPa, or about 0.1 mPa to about 1 mPa, as illustrative examples. A range of acoustic signal can vary and be selected based on the properties and characteristics of affected area and/or medium in which the magnetic nanoparticles are placed. For example, a more severe thrombosis may require a more intense acoustic signal. Or as another example, a stronger acoustic signal can be applied near a subject's heart, but a less intense acoustic signal may be required for a subject's brain.

A frequency of the alternating current signal 200 is generally in a range of about 50 Hz to about 5 MHz. In one embodiment, the frequency of alternating current is about 50 Hz to about 200 Hz (the doubled acoustic frequency would then be about 100 Hz to about 400 Hz). In another embodiment, the frequency of the alternating current signal is about 150 Hz to about 500 KHz (doubled acoustic frequency of about 300 Hz to about 1 MHz). In still another embodiment, the alternating current signal frequency is about 500 KHz to 5 MHz (doubled acoustic frequency of about 1 MHz to about 10 MHz). A combination of frequency components may be delivered to the magnetizing coil. In one embodiment, two frequencies are combined including a resonance frequency and an effective frequency, f, which is generated by minimum energy and can be calculated using the equation:

$$f = \frac{1}{2\pi}\sqrt{\frac{k}{m}}$$

where k indicates elastic coefficient and m indicates mass.

Finally, it is possible to determine the velocity, magnetic field, and magnetic gradient once the distance between the magnetic nanoparticles and the magnetizing coil is known. This makes it possible to control these aspects precisely to enhance safety to the subject to which the treatment is being applied. Since from above, the magnetic force on the magnetic nanoparticles is:

$$F = \mu_0 (\chi_P - \chi_f) V H \frac{\partial H}{\partial x}$$

where $\mu_0$ indicates space permeability, $X_p$ is a volume magnetic susceptibility of the magnetic nanoparticles, $X_f$ is a volume magnetic susceptibility of the medium, V indicates volume of the site, H indicates the strength of the magnetic field, and $\partial H/\partial x$ indicates a local magnetic gradient, and using Stoke's law, $$F_v = 6\pi\eta r v$$

where v indicates a speed of the magnetic nanoparticles, $\eta$ indicates a viscosity of a medium in which the magnetic nanoparticles are placed, and r indicates a radius of each magnetic nanoparticle, then velocity, v, can be calculated as $$v = \frac{2\mu_0 (\chi_P - \chi_f) r^2}{9\eta} H \frac{\partial H}{\partial x}$$

The above equation indicates that terminal velocity is determined by viscosity. However, the velocity can be increased and work increased if the magnetic field, H, and the magnetic gradient $\partial H/\partial x$ is more intense. The more intense the magnetic field, H, becomes, the more gets harmful to a subject. However, the technology disclosed herein provides additional safety since the magnetic field intensity does not rise to levels that would be harmful to biological subjects. That is because the magnetic field and magnetic gradient required to set a frequency of an acoustic signal to about double a frequency of the alternating current only requires up to about 5 MHz, which is well under the range of what would be harmful to biological subjects. Therefore, the above equation allows a technician to determine the appropriate velocity, magnetic field, and magnetic gradient. That is, velocity is determined by magnetic field and magnetic gradient. And since magnetic field and magnetic gradient are controlled by an electric current, the velocity, magnetic field and magnetic gradient can all be controlled by controlling the electric current. This makes this technology easy to control precisely, which can be beneficial especially in medical applications.

Embodiments for applying an alternating magnetic field include using a magnetizing coil to generate or excite an alternating magnetic field to be applied to the magnetic nanoparticles. The size of a wire forming the magnetizing coil may have a diameter of about 0.4 mm to about 1 mm, or from about 0.4 mm to about 4 mm, as illustrative examples. The size of wire forming the magnetizing coil depends on a volume of applied electric current. The magnetizing coil may also be formed from a number of turns. The electricity, i, to generate a magnetic field intensity H is inversely proportional to the square of the magnetizing coil turns n. In one embodiment, a diameter of a coil turn of a magnetizing coil may be less than 60 cm, or from about 1 cm to about 25 cm, or from about 1 cm to about 10 cm, as illustrative examples. As noted below, one aspect of the magnetizing coil is that the subject does not have be placed within the center of the magnetizing coil, as must normally be done with conventional magnetic field generators. So the magnetizing coil can generally be much smaller than has conventionally been required. Various metals can be used for the magnetizing coil including, but not limited to, copper (Cu), aluminum (Al), silver (Ag), and platinum (Pt) and the like or a combination thereof. Also superconductive coils such as niobium (Nb) and lead (Pb) may be used. Generally, wires can be purchased and then made into coils with the desired number of coil turns. Alternatively, magnetizing coils can be purchased already manufactured having a standard wire size and number of coil turns, and optionally, a metal core (described below).

The magnetizing coil may also include a hollow core. In other embodiments, the magnetizing coil may have a metal core. For example, a ferrite core decreases the number of coils required for the magnetizing coil, while generating a magnetic field having the same amplitude as a coil with a hollow core and using a tenth of the electricity. Thus using a metal core can decrease the number of turns of the magnetizing coil and, hence, the total length of the wiring material. This can also reduce the amount of direct resistance in the coil as well as reduce copper loss.

The magnetizing coil turns may be from 1 to 100 turns, or from 1 turn to 50 turns, or from 1 turn to 15 turns, or from 5 turns to 100 turns, or from 5 turns to 50 turns, or from 5 turns to 15 turns, as illustrative examples. The number of turns depends on the frequency of the alternating current and/or the diameter of a coil turn. For example, for 1 MHz current in a wire having a coil turn diameter of about 10 cm, the magnetizing coil may have 12 coil turns. For a frequency of alternating current of 100 Hz, for a wire having a coil turn diameter of about 10 cm, the magnetizing coil may have 200 turns, but may have considerable weight.

When the magnetizing coil has a hollow core and a single turn, the generated magnetic field is calculated by the equation $$B_z(z) = \frac{\mu_0 I_1 a^2}{2(a^2 + z^2)^{3/2}}$$

-continued $$\mu_0 = 4\pi \times 10^{-7} = 1.2566370614 \ldots \times 10^{-6} \; [H/m]$$

where $\alpha$ is radius, z is a direction from the center of the magnetizing coil toward axis direction, $\mu_0$ is space permeability and $I_1$ is coil current. When the number of coil turns is n, the magnetic field can be approximated to n times.

When there is a core in a magnetizing coil, the magnetic flux calculated above is pulled into the core. In one embodiment, the length of the core is 6 times longer than the diameter of the core. In one embodiment, a ferrite core can be used having a 30 mm² diameter square area and 10 cm length.

In one embodiment, the alternating magnetic field has a magnetic induction that may be from about 2 mT to about 80 mT (Tesla: 1 mT=10 Gauss). For hyperthermia treatments, the alternating magnetic field may be about 10 mT to about 15 mT, while for thrombolysis treatments, the alternating magnetic field may be in a lower range than for hyperthermia treatments. In embodiments where the alternating magnetic field includes an alternating current component and a direct current component, the alternating current component may be from about 2 mT to about 5 mT and the direct current component may be about 10 mT to about 50 mT.

Figure 3:
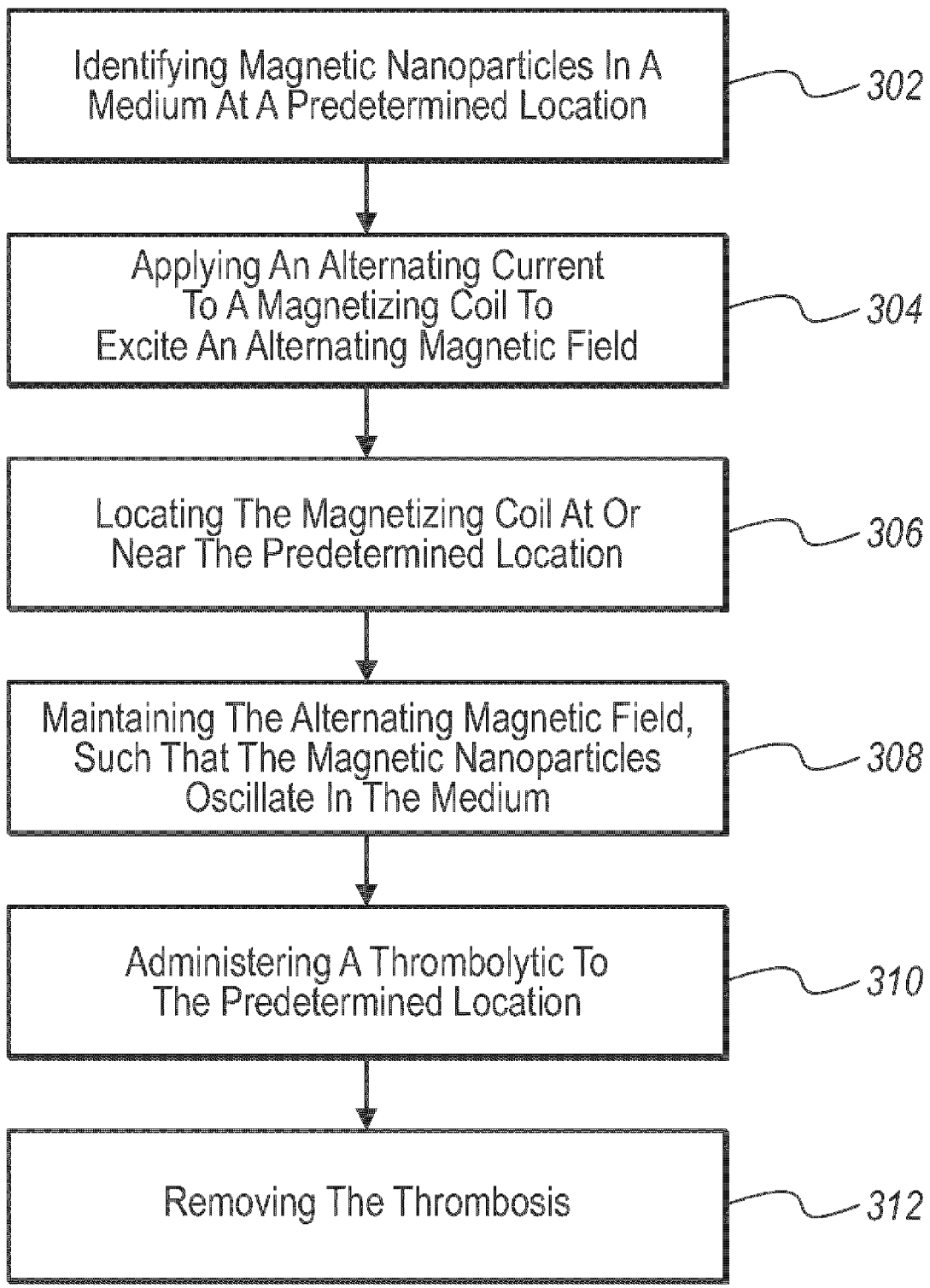
FIG. 3 is a flow diagram showing an illustrative embodiment of a method for activating magnetic nanoparticles.

FIG. 3 is a flow diagram showing an embodiment of a method for activating magnetic nanoparticles. In one embodiment, the magnetic nanoparticle is optionally selected or configured to create the appropriate amount of resistance between the magnetic nanoparticle and medium. This can include selecting magnetic nanoparticle of a particular size, or placing a coating on at least a portion of the magnetic nanoparticle with a resistance generating or a resistance decreasing structure. The resistance generating or resistance decreasing structure of the coating of the magnetic nanoparticle allows the medium with the affected area and the magnetic nanoparticles to more effectively use the momentum of the magnetic nanoparticle to generate energy, creating an acoustic signal and/or heat. In one embodiment, the resistance generating or decreasing structure provides a steric structure to be more three-dimensional or less three-dimensional to increase or decrease resistance, respectively. Therefore, a magnetic nanoparticle can be optimally selected to result in better treatments.

Further, ferromagnetic and ferrimagnetic magnetic nanoparticles tend to lose their magnetization which can cause the magnetic nanoparticles to aggregate under an intense magnetic field. When magnetic nanoparticles aggregate, their magnetic susceptibility decreases. Thus, magnetic force F decreases when magnetic nanoparticles aggregate. Embodiments include using magnetic nanoparticles having superparamagnetic characteristics such that under a weak magnetic field (such as <2 mT (30G)) the magnetic nanoparticles will not aggregate and can be more effective when a stronger alternating magnetic field is applied.

At 302, the method includes optionally identifying one or more magnetic nanoparticles in a medium at a predetermined location. The term "identifying" generally refers to knowing the predetermined location in which the magnetic nanoparticles have been placed at a prior point in time, actually placing the magnetic nanoparticles at a predetermined location, or detecting the presence and/or location of one or more magnetic nanoparticles through detection methods known and/or disclosed herein. In one embodiment, this can include injecting magnetic nanoparticles in the medium at the predetermined location, which can be a site being treated for thrombosis, hyperthermia, various types of thrombus, or other medical treatments, and the like. As discussed above, this method breaks and/or removes thrombosis or destroys tumor by hyperthermia as an efficient medical treatment. In illustrative embodiments, the magnetic nanoparticles may be injected intravenously, or may be injected in the plaque directly using a catheter. In one embodiment, the magnetic nanoparticles can be tracked via X-ray, electrocardiogram, or also fluorescent markers.

At 304, the method includes applying or generating an alternating current through a magnetizing coil to excite an alternating magnetic field of the magnetizing coil.

At 306, the method optionally includes placing the magnetizing coil having the alternating magnetic field near the predetermined location.

At 308, the method optionally includes maintaining the alternating magnetic field for a period of time, wherein the one or more magnetic nanoparticles oscillate in the medium at the predetermined location. The period of time may depend on the purpose for which the magnetic nanoparticles are being used, a seriousness of condition of the affected area, how quickly a doubled acoustic frequency is detected, and the like. During the period of maintaining the alternating magnetic field, the intensity of the alternating magnet field may change, or it may remain the same. As discussed above, oscillation can occur in both the transverse and longitudinal directions that enables the magnetic nanoparticles to be more active in motion compared with an oscillation by direct excitation so that the magnetic nanoparticles break thrombus plaques more strongly.

At 310, embodiments optionally include administering a thrombolytic to the predetermined location. Adding a thrombolytic to a site where the magnetic nanoparticles are located can enhance the breaking effect by assisting to dissolve the media, allowing the magnetic nanoparticles to move with more freedom. The type of thrombolytic may depend on the particular treatment site. Examples of thrombolytics that could be used include, but are not limited to, tissue plasminogen activator (t-PA), urokinase (u-PA), streptokinase, and the like. Thrombolytics can be administered by injecting intravenously, local injection, by catheter, and the like. The thrombolytic may be administered prior to treatment with magnetic nanoparticles, during treatment of magnetic nanoparticles, and/or after treatment with magnetic nanoparticles. The amount of thrombolytic administered also depends on the particular treatment site, the purpose for which the magnetic nanoparticles are being used, a seriousness of condition of the affected area, and the like.

At 312, the method may also include using a catheter to remove the thrombosis. In embodiments where the method treats various types of thrombus, this method can be used for removing intracoronary thrombus. The plaques formed in coronary arteries are thought to be a major cause of ischemic cardiac diseases, which can cause Transient Ischemic Attack (TIA). Especially atherothromobosis causes Acute Coronary Syndrome (ACS) and it is strongly desired to establish an efficient treatment for this disease. The above method is believed to be effective in treating these types of diseases.

In one embodiment, the magnetic nanoparticle treatments can be used in conjunction with other therapies or treatments. For example, balloon catheters and stents are frequently used to remove thrombus. A balloon catheter is a balloon inserted by a catheter to a predetermined location (usually a blood vessel) containing thrombus. The balloon is then expanded to help break up the thrombus. A stent is a related procedure in which a stent is inserted by a catheter to a predetermined location (usually a blood vessel). The stent is then expanded and can assist to remove the thrombus. The stent can also be left inside the blood vessel to provide reinforcing structure to the blood vessel walls. Embodiments disclosed herein can be combined efficiently with these other therapies or treatments. For example, for balloon catheters, the magnetic nanoparticle treatment could be applied using the same catheter that is used to perform the balloon catheter treatment. For stents, the magnetic nanoparticle treatment can be performed before implementing a stent and using the same catheter. In yet another embodiment, thrombolytics could also be applied through the stent. Other variations will be apparent based on the disclosure herein.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Magnetic field generating devices such as an MRI that generate a direct magnetic field using a circular coil requires the subject to be placed within the circular coil in the middle of the magnetizing coil. In other words, the subject passes through a plane area formed by the magnetizing coil. Conventionally, a size of the magnetizing coil needed to be large to be able to set the subject (e.g., human patient) within the magnetizing coil. As the size of the magnetizing coil increases, its inductance and impedance also increase, which also increases a resistance and amount of heat generated. To solve this problem, conventionally, the magnetizing coil needed to be cooled down, prolonging the amount of time for the treatment and requiring extra process steps. Further, a larger coil size was more cumbersome to handle and operate, introducing inconveniences to both the patient and the medical technician.

Embodiments herein provide methods of treatment in which the subject does not have to be placed within the magnetizing coil, yet still provides enhanced movement of the magnetic nanoparticles. In other words, embodiments provide that the subject does not pass through a plane area formed by the magnetizing coil. In some embodiments, the magnetizing coil can be applied near the affected area in a manner that maximizes acceleration of the magnetic nanoparticles. Embodiments herein obtain better momentum of the magnetic nanoparticles while using a coil turn having a smaller diameter than has conventionally been required. By being able to use a smaller diameter coil turn, the magnetizing coil does not heat as quickly, thus eliminating cooling steps that have conventionally been required. Further, the magnetizing coil does not endanger the subject, especially where the magnetizing coil is being applied on a biosystem (e.g., a human).

FIGS. 4A through 4D are graphs showing a correlation between an alternating current signal and an acoustic signal taken at various detection points. FIGS. 4A through 4D illustrate the effect of locating a magnetizing coil in various positions with respect to a cluster of magnetic nanoparticles. Each of FIGS. 4A through 4D shows an excited alternating current signal 400 (shown as a dashed line) and an elastic wave or acoustic signal 402A-D (shown in a solid line) generated by the magnetic nanoparticles when an alternating magnetic field is applied to the magnetic nanoparticles.

Figure 4B:
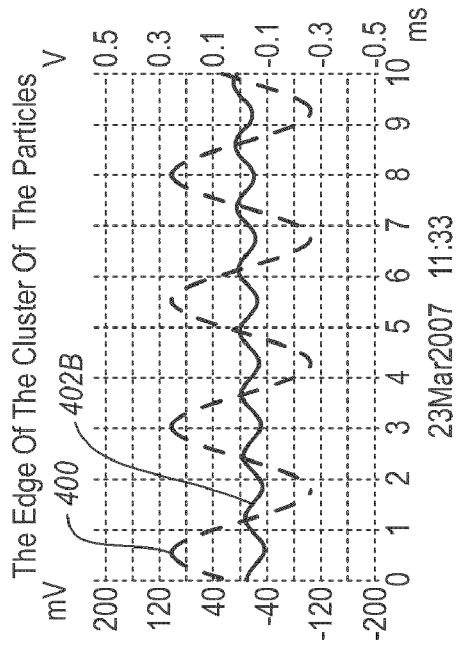
FIGS. 4A through 4D are graphs showing an illustrative embodiment of a correlation between an excited alternating current signal and an acoustic signal from various detection points.
Figure 4D:
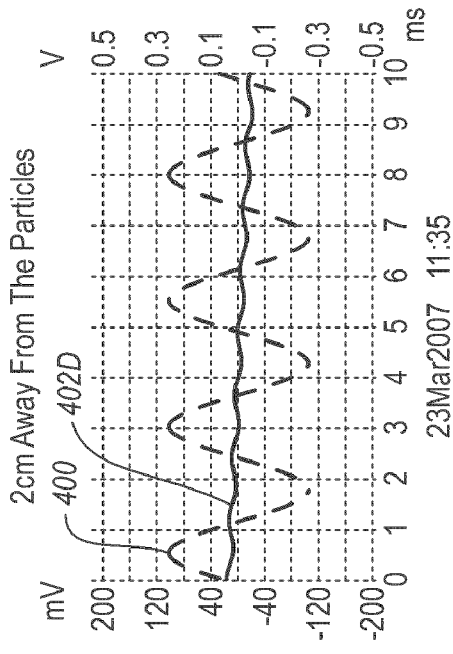
Figure 4A:
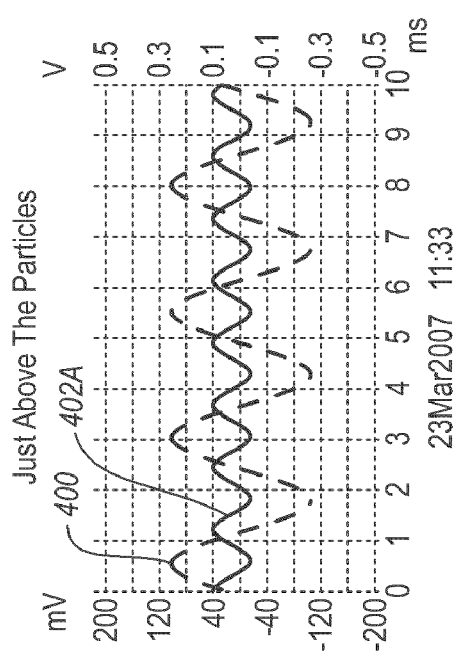
Figure 4C:
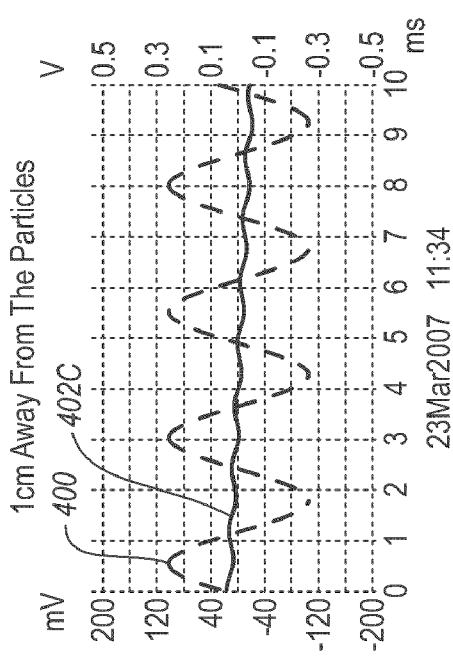

FIG. 4A shows graphically the alternating current signal 400 and acoustic signal 402A when the magnetizing coil is applied just above the particles. FIG. 4B shows the alternating current signal 400 and acoustic signal 402B when the magnetizing coil is located at the edge of the cluster of the magnetic nanoparticles. FIG. 4C shows the alternating current signal 400 and acoustic signal 402C when the magnetizing coil is located about 1 cm away from the magnetic nanoparticles. FIG. 4D shows the alternating current signal 400 and acoustic signal 402D when the magnetizing coil is located about 2 cm away from the particles. By being able to measure the frequency of the acoustic signal 402A-D as compared to the frequency of the alternating current signal 400, the technician will be able to determine when the magnetizing coil is located just above the particles. For example, if a 10 cm diameter magnetizing coil is located 2 cm away from the predetermined location where magnetic nanoparticles are located, the technician is able to simply check the waveform of the alternating current signal 400 as compared to the acoustic signal 402D.

The difference in the wave forms of FIGS. 4A through 4D are a result of sound attenuation at various locations in the medium. As the acoustic probe moves farther from the magnetic nanoparticles, the sound attenuates gradually by absorption damping effects of the medium. Therefore, the amplitude of the acoustic signal gets smaller as the acoustic probe moves away from the sound source (i.e., the magnetic nanoparticles).

Noise and phase shift can complicate measuring the acoustic signal. The magnetizing coil resonates at the same frequency of the alternating frequency and generate noise, which noise can be filtered out. Acoustic sound in the ultrasonic region generates a less intense acoustic signal. However, there are fewer noises such as motion of organs, heart beats, and respiratory sound that need to be filtered out. Also frequencies of the alternating signal and the doubled acoustic signal are sufficiently apart so that they can be isolated well. A double frequency synchronous cross-detector extracts the amplitude value and phase accurately of the acoustic signal.

In general, coronary arteries are located around 9 cm deep from the body surface at deepest. Even at that distance, the magnetic nanoparticles can be injected and oscillated by applying an alternating magnetic field. In one embodiment, the alternating magnetic field is less than 10 mT. In another embodiment, the alternating magnetic field is about 3 mT. FIGS. 4A through 4D thus illustrate one type of measurement that can be used to compare the location of the magnetizing coil with respect to the magnetic nanoparticles.

Figure 5:
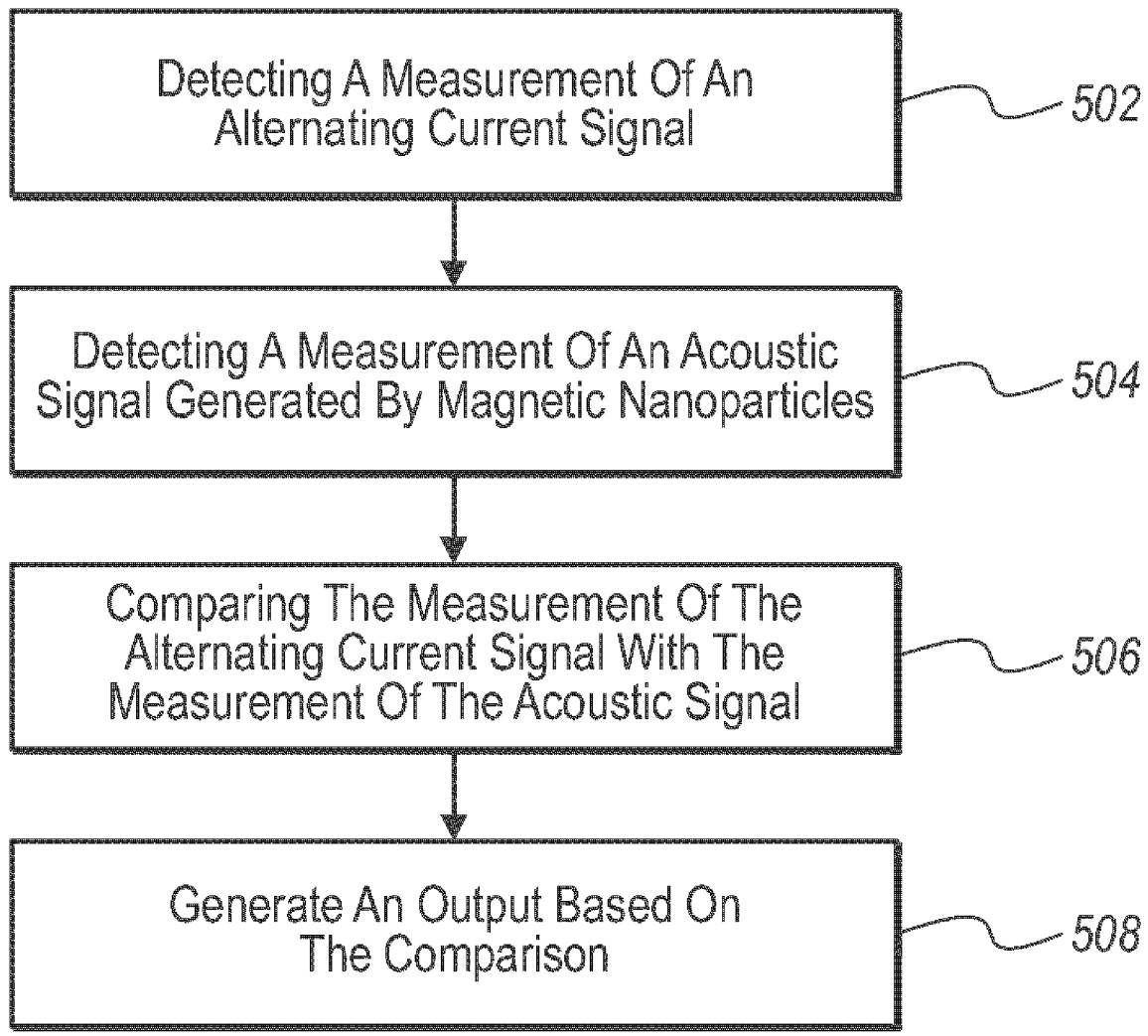
FIG. 5 is a flow diagram of an illustrative embodiment of a method for determining location of a magnetizing coil with respect to magnetic nanoparticles.

FIG. 5 illustrates a flow diagram of one embodiment of a method for determining the location of the magnetizing coil with respect to the magnetic nanoparticles. Initially, a technician will place a magnetizing coil within proximity of a cluster of magnetic nanoparticles. At 502, a detecting device (described below) detects a measurement of an alternating current signal, and, at 504, the same or different detecting device detects a measurement of an acoustic signal. For example, the measurement of the alternating current signal may be a frequency of the alternating current signal and the measurement of the acoustic may be a frequency of the acoustic signal. In one embodiment, the method can include processing the acoustic signal with a pre-amplifier. At 506, the detecting device compares the measurement of the alternating current signal with the measurement of the acoustic signal. For example, in one embodiment, the detecting device may determine whether the frequency of the acoustic signal is about double the frequency of the alternating current signal.

At 508, the detecting device generates an output based on the comparison. For example, in one embodiment, the output is a graphical representation of the comparison of the measurement of the alternating current signal and the measurement of the acoustic signal (see FIG. 2). In one embodiment, a technician uses the graphical comparison to determine a positioning of the magnetizing coil with respect to the magnetic nanoparticles. In one embodiment, this can include displaying whether the frequency of the acoustic signal is or is not substantially double the frequency of the alternating current signal. This allows a technician to decide whether to reposition the magnetizing coil. In another embodiment, the output can reflect an intensity of the alternating current signal and/or acoustic signal. A technician could then adjust an intensity of the alternating current signal. Or, an apparatus or computer device disclosed herein could be configured to automatically adjust an intensity of the alternating current signal. In still another embodiment, the output could also be used to determine an amount of electric current to obtain a particular magnetic field strength using the distance between the magnetizing coil and particles, the measurement of the alternating current signal and the measurement of the acoustic signal. Other optimization of the process can be performed as will be understood by those skilled in the art based on the disclosure herein.

Although not shown in FIG. 5, the method can further include searching an oscillation of a frequency as doubled as the frequency of the magnetic field (i.e., a doubled frequency), processing the doubled frequency with a pre-amplifier, and detecting a part oscillating the doubled frequency with a double frequency synchronous cross-detector to isolate the acoustic signal.

While the method of FIG. 5 shows the measurement being a frequency of an alternating current signal and a frequency of an acoustic signal, other measurements can be used to detect the position of the magnetizing coil. In one embodiment, phase shifting can be used to determine the location of the magnetizing nanoparticles. Since acoustic sounds generated by the magnetic nanoparticles will experience a phase difference depending on the speed of sound and time of transmission, a measurement of one acoustic frequency indicates linear distance. Measurement of plural acoustic frequencies thus determines very accurate linear distance. Further, when more than three wave receivers are placed on a body surface, aperture synthesis enables a technician to determine a 3-dimensional positioning with a high degree of accuracy.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 6A:
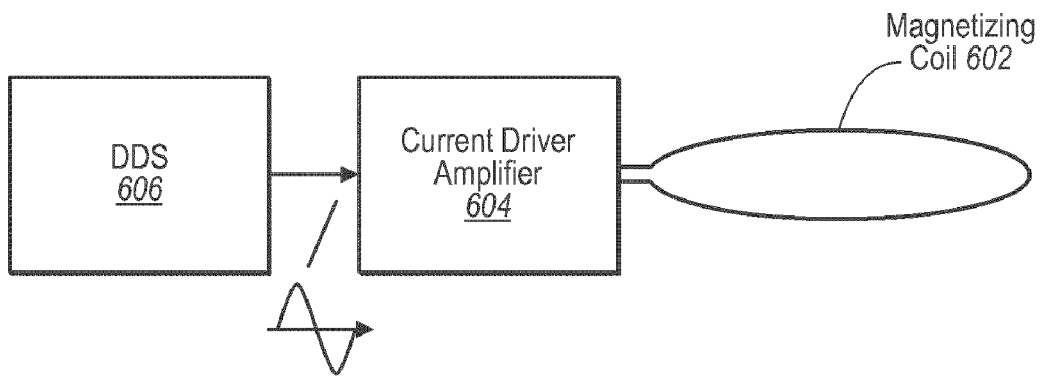
FIG. 6A is a schematic view of an illustrative embodiment of an apparatus for generating an alternating magnetic field according to an embodiment.

FIG. 6A is a schematic view of an apparatus 600A for generating an alternating magnetic field according to one embodiment. As shown in FIG. 6A, a magnetizing coil 602 is connected to a current driver amplifier 604, which, in turn, is connected to a direct digital synthesizer or function generator 606. During operation, the current driver amplifier 604 and direct digital synthesizer 606 operate together to apply or generate an alternating current within magnetizing coil 602. The magnetizing coil 602 can then be applied near an affected area to activate magnetic nanoparticles located at the affected area.

Figure 6B:
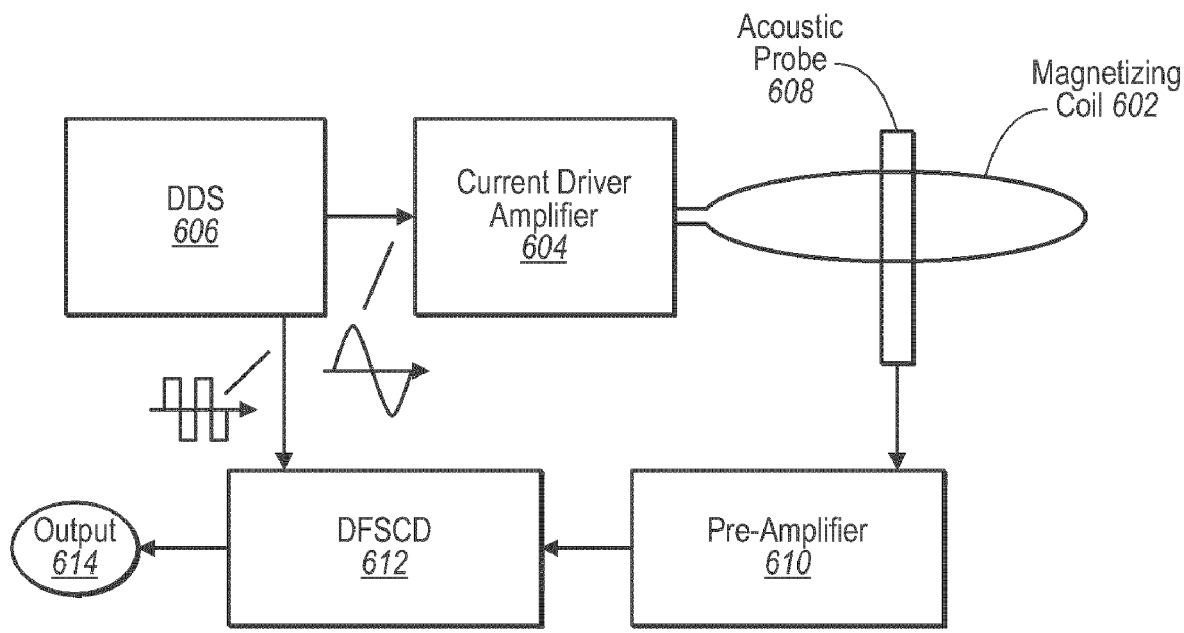
FIG. 6B is a schematic view of an illustrative embodiment of an apparatus for generating an alternating magnetic field and detecting an acoustic signal according to an embodiment.

FIG. 6B is a schematic view of an apparatus 600B for generating an alternating magnetic field and detecting an acoustic signal according to another embodiment. Like elements will be referred to with like reference numerals. FIG. 6B shows a magnetizing coil 602, current driver amplifier 604 and direct digital synthesizer 606 in operable connection similar to FIG. 6A.

The apparatus 600B is able to also detect acoustic signals generated by the magnetic nanoparticles. Hence, an acoustic probe 608 is connected to a preamplifier 610 which, in turn, communicates with a double frequency synchronous cross-detector 612. The acoustic probe 608 measures an acoustic signal generated by magnetic nanoparticles when they are oscillated by an alternating current. The preamplifier 610 is able to amplify the acoustic signal and send the amplified acoustic signal to the cross-detector. The direct digital synthesizer 606 sends an indication of a frequency of the alternating current signal to the cross-detector 612. In this manner, the cross-detector 612 analyzes the input received from the direct digital synthesizer 606 and the input from the preamplifier 610 to determine whether the frequency of the alternating current signal is about double the frequency of the acoustic signal. The cross-detector 612 is able to provide an output 614. One embodiment of an output 614 could be a display on a graphical user interface displaying the alternating current signal and the acoustic signal, similar to what is shown in FIGS. 4A through 4D. In other embodiment, output 614 can include a graphic notification, audible notification, or other manner of indicating whether the magnetizing coil is within a desired range of proximity of the magnetic nanoparticles.

Figure 7:
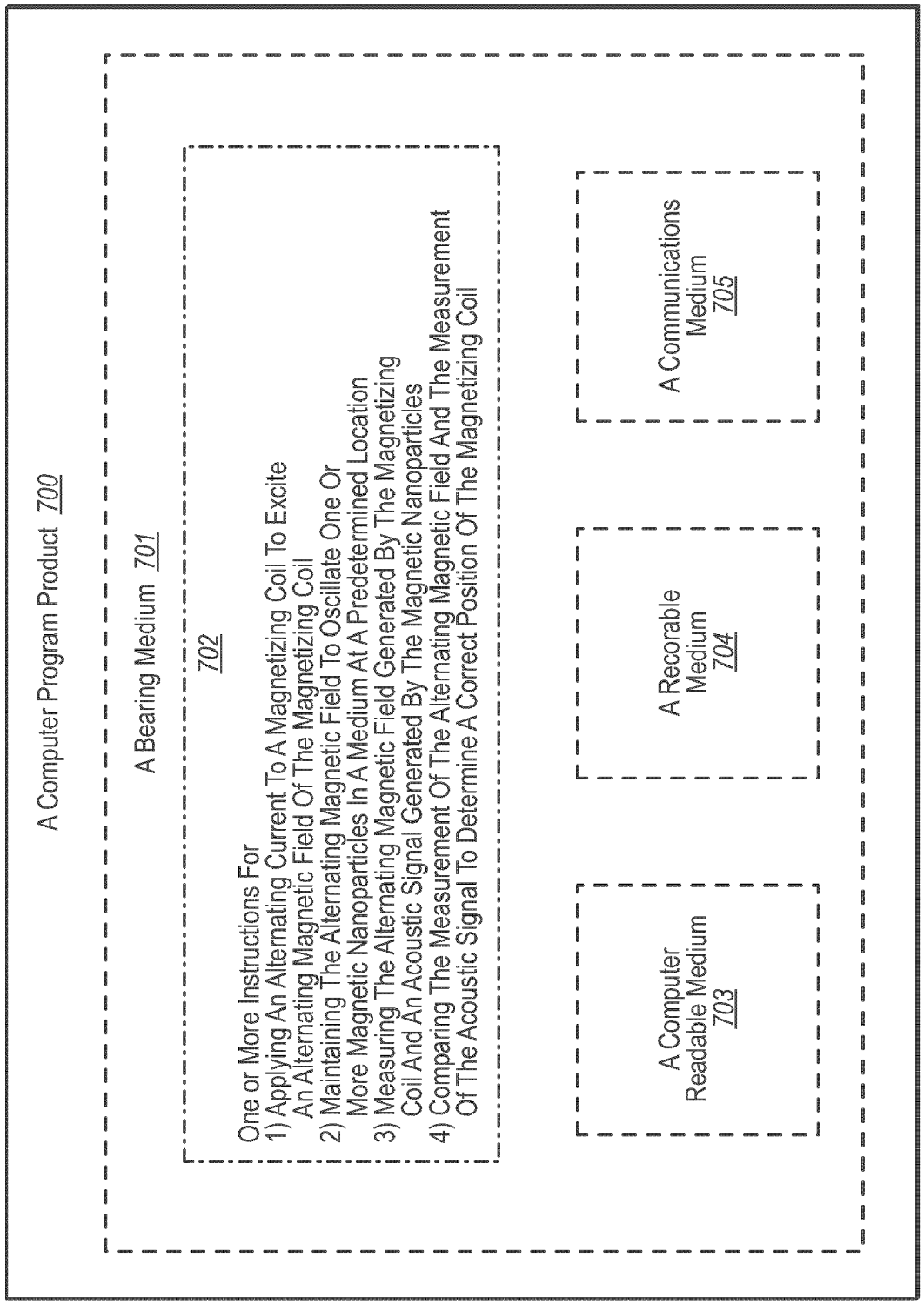
FIG. 7 is a schematic view of an illustrative embodiment of a computer program product.
Figure 8:
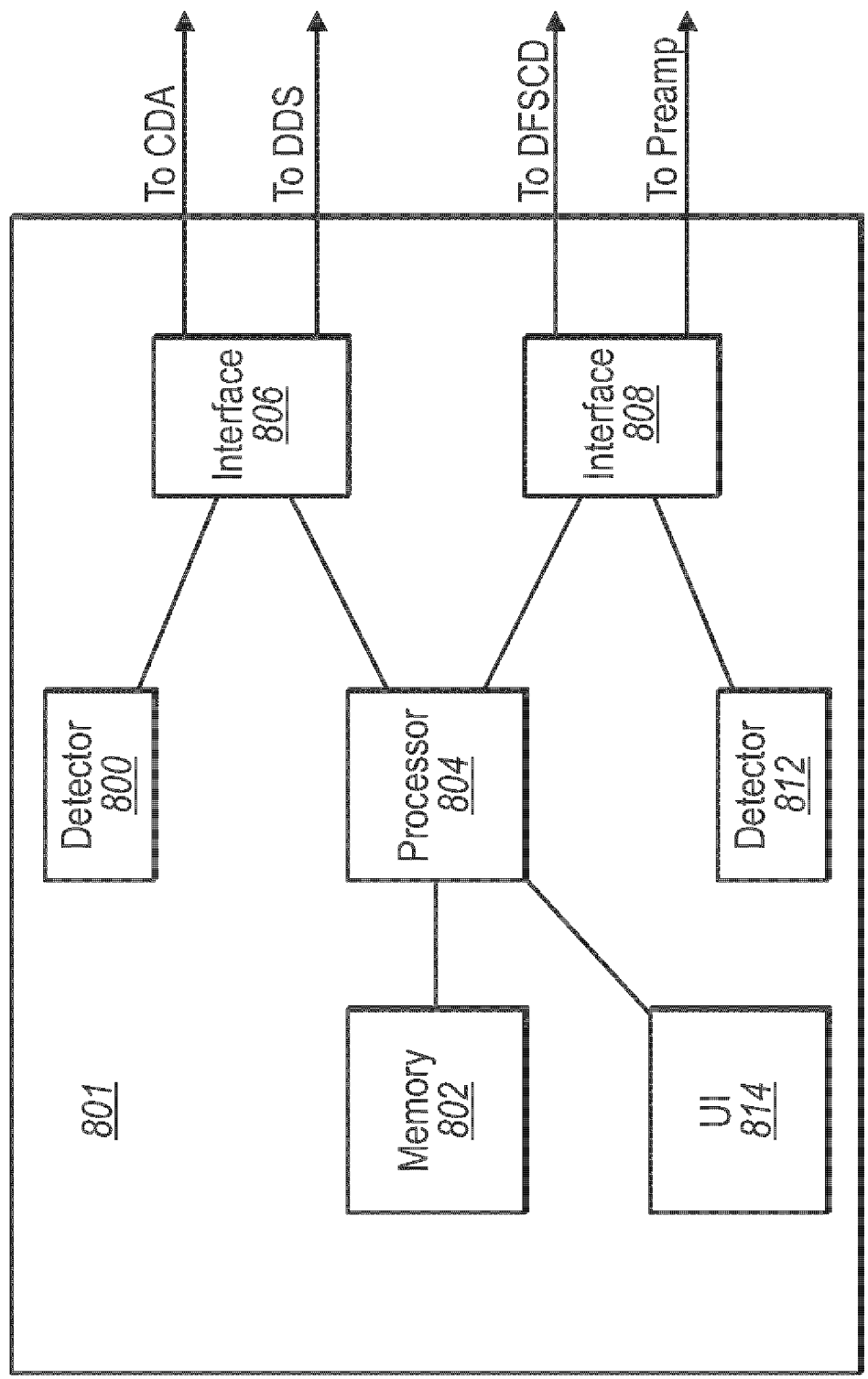
FIG. 8 is a schematic view of an illustrative embodiment of a computer system.

The embodiments shown in FIGS. 6A and 6B can be implemented in a computer environment, as shown in FIGS. 7 and 8, which are examples of a computer program product and computer system, respectively. FIG. 7 shows a schematic view of an illustrative computer program product 700 that includes a computing program for executing a computer process on a computing device for a medical treatment. The computer program is provided using a signal bearing medium 701, and may include at least one instruction of 702: providing an alternating current to a magnetizing coil, exciting the magnetizing coil to generate an alternating magnetic field to oscillate magnetic nanoparticles located within a medium, measuring a frequency of the alternating current signal and a frequency of an acoustic signal generated by the oscillating magnetic nanoparticles, and comparing the frequency of the alternating current signal with the frequency of the acoustic signal. In some embodiments, the signal bearing medium 701 of the one or more computer program products 700 include a computer readable medium 703, a recordable medium 704, and a communications medium 705.

FIG. 8 shows a schematic view of an illustrative computer system for a medical treatment in which embodiments may be implemented. The system may include a computing system environment. The system includes a computing device 801. The computing device 801 includes a memory 802 containing one or more instructions that when executed by a processor 804 on the computing device 801 cause the computing device 801 to apply or generate an alternating current to a magnetizing coil to generate an alternating magnetic field. The computer device 801 can operate, for example, in conjunction with apparatuses shown in FIGS. 6A and 6B and thus includes inputs/outputs and/or appropriate interfaces for communicating with aspects of the apparatuses shown in FIGS. 6A and 6B. For example, computer device 801 can include an interface 806 that communicates with a direct digital synthesizer and/or current driver amplifier to control the operation thereof.

In the embodiment of FIG. 8, the computer device 801 can include a second interface 808 that communicates with a double frequency synchronous cross-detector and/or preamplifier. The computer device 801 can also include a first detector 800 for measuring a frequency of an alternating magnetic field generated by the direct digital synthesizer and current driver amplifier and a second detector 812 for measuring an acoustic signal detected by the acoustic probe, preamplifier and double frequency synchronous cross-detector. The processor 804 can then take the input from the detectors 800 and 812 to perform a comparison process on the inputs and determine whether the magnetizing coil is located in the correct location. In one embodiment, the processor 804 can display graphically the inputs on a graphical user interface 814. Although not shown, the computer device 801 can also include user input means to control the operation of the computer device and/or apparatus, such as, but not limited to, keyboards, touch screens, buttons, microphone, mouse, and the like. Using this computing device 801 with the method and apparatus of this disclosure, medical providers are able to provide better treatment methods for thrombosis, hyperthermia and so on. In one embodiment, the components of computer device 801 can be distributed on separate systems. In another embodiment, the components of the computer device 801 can be integrated into a single system. In addition, some of the components can be combined, although shown separately in the drawing. For example, in one embodiment, the first detector 800 and second detector 812 could be the same component.

Figure 9:
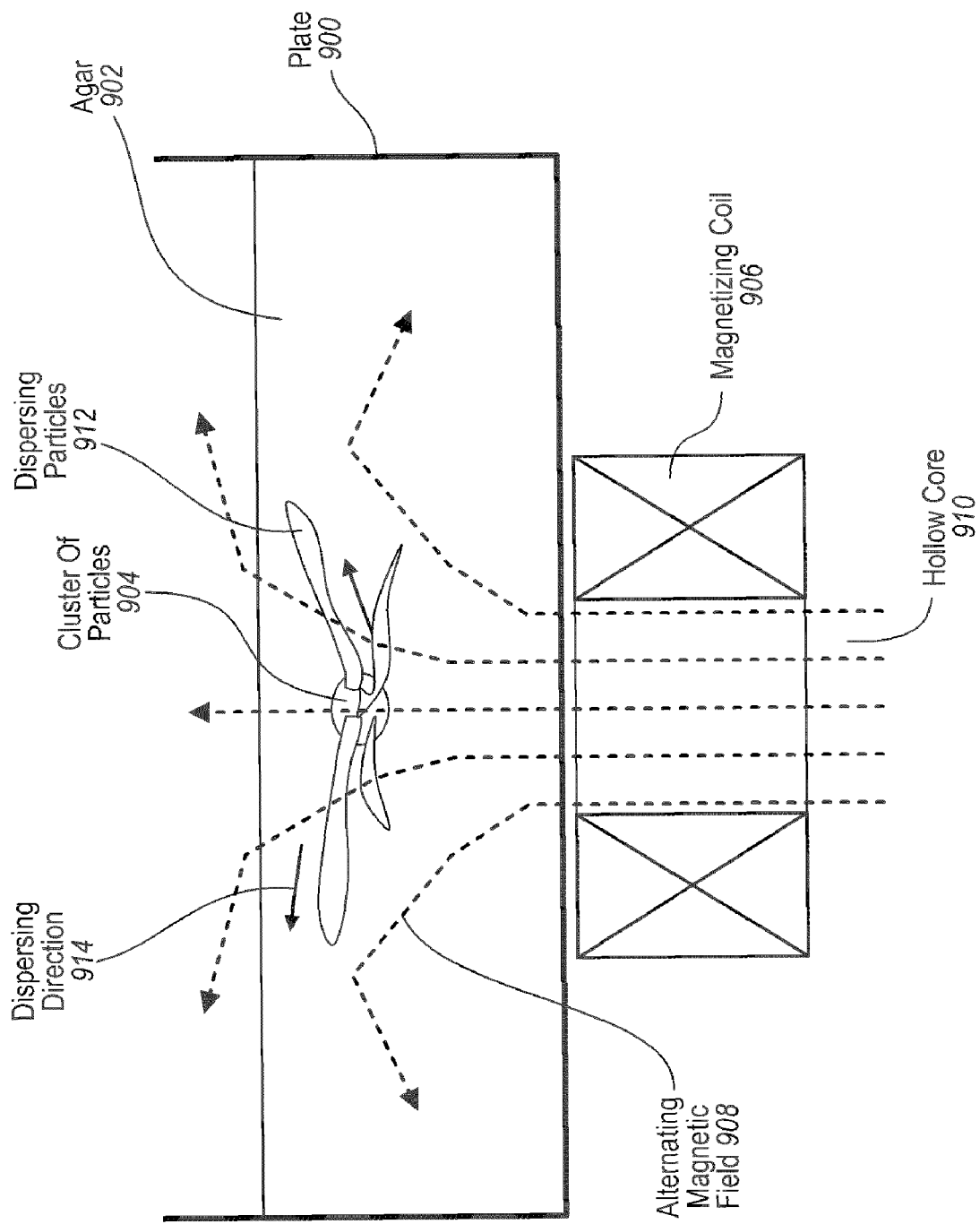
FIG. 9 is a configuration of an illustrative embodiment of an experiment.

FIG. 9 shows a configuration of an experiment according to an embodiment to evaluate the destructive capabilities of the magnetic nanoparticles in pseudo-plaque when using teachings of this disclosure. In FIG. 9, magnetic nanoparticles were placed in agar and dispersed by an alternating magnetic field generated by a magnetizing coil. Thus, the agar was used as a pseudo-plaque medium.

Preparation of Agar as a Pseudoplaque

The preparation was done as follows: An amount of water was heated to exceed 60° C. Gradually added agar and stirred to make 1% agar. Boiled agar solution to about 85° C. to 95° C. for de-gassing. Maintained agar solution for 5 to 10 minutes and then allowed to cool in ambient air until the temperature of the solution reached 55° C. During this period, broke any air bubbles that appear (e.g., using tweezers). Continued to stir slowly to prevent agar surface from becoming hardened. When reached 55° C., poured agar solution into a container and allowed to cool in ambient air to harden agar.

The agar was poured into the container in two stages. In the first stage, a first layer of agar was poured to a desired height at which the thrombosis was to be located and allowed to cool (about 1 hour). The thrombosis was then placed on top of the hardened first layer. A second layer of agar was poured over the first layer and the thrombosis and allowed to cool (about 1 hour).

The Components of the Apparatus

Although not shown in FIG. 9, the apparatus used contained the following components:

Magnetic nanoparticle: supplied by Shering AG company and sold under the trademark Resovist®

Magnetizing coil: constructed of 0.4 mm diameter copper wire with 35 turns, each turn being about 10 cm in diameter.

Direct Digital Synthesizer self-manufactured using Max II series CPLD (Altera Corp., San Jose, Calif.) and PDM Digital-to-Analog convertor using Pulse Density Modulation technology to generate output and electron volume, applying alternating current signal frequency of 500 Hz Current driver amplifier: self-manufactured using a volt-ampere converter using Power OP amplifier OPA541 or LM675 (Max±2Z) applying alternating current of 300 mA Acoustic probe self-manufactured: processing a resin with a lathe and using a condenser microphone for the detector/sensor Preamplifier: self-manufactured using a Sigma-Delta type A/D converter set up by AD822 and input into CPLD. Digital synchronous wave detecting circuit is set up using 2-phase square wave provided from (Direct Digital Synthesizer) DDS internally.

Double frequency synchronous cross detector: self manufactured using a Sigma Delta to convert the wave into a PDM (pulse density modulation) binary signal. A multiplication circuit processes the binary signal. A detecting wave circuit includes a counter that calculates the number of pulses per unit time.

Monitoring the Acoustic Signal from the Magnetic Nanoparticles

Using the agar plate, the monitor test was carried out. As shown in FIG. 9, a plate 900 was prepared containing agar 902 as a pseudoplaque. The thrombosis plaque was formed by dropping alginic acid into a solution of calcium chloride drop by drop. Magnetic fluid containing magnetic nanoparticles was injected into the thrombosis plaque held in the agar 902 as cluster 904 of about 3 mm diameter. The cluster 904 was injected about 30 mm deep from the bottom surface of the agar 902 and about 10 mm from the top surface of the agar.

Then, a magnetizing coil 906 was set under the agar plate 900, as shown in FIG. 9 and the acoustic probe (not shown) was put on the agar surface and the direct digital synthesizer (not shown) was turned on. While the magnetizing coil 906 was generating a magnetic field 908, the probe was moved slowly on the surface of the agar and detected a change of the doubled frequency. The results are shown in FIGS. 2 and 4A through 4D. Particularly, FIGS. 4A through 4D show graphs of detecting the acoustic signal when the acoustic probe is located in various locations. This experiment shows that the acoustic probe can detect the location of the magnetic nanoparticles according to the pattern of the acoustic signal generated by the magnetic nanoparticles.

Destruction Test

As shown in FIG. 9, the magnetizing coil 906 with a hollow core 910 was set below the agar plate 900. Same as the monitoring test above, the magnetic nanoparticles were injected as a cluster 904 into the agar 902. The magnetizing coil 906 was excited with alternating current so as to generate a 3 mT (30 G) alternating magnetic field 908. The alternating magnetic field 908 was maintained for about 2 minutes to about 10 minutes at about 3 mT. While the alternating magnetic field 908 was applied to the agar 902, the cluster 904 magnetic nanoparticles were gradually dispersing in the agar 902 and broke up the agar. The broken up agar is represented in FIG. 9 by the portions of dispersing particles 912 being shown as moving in various dispersing directions 914.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:
1. A method for a medical treatment comprising:
applying an alternating current signal to a magnetizing coil in order to excite an alternating magnetic field near one or more magnetic nanoparticles at a first location, the alternating magnetic field effective to increase an oscil- lation of the one or more magnetic nanoparticles at the first location and generate an acoustic signal;
detecting the acoustic signal;
comparing the detected acoustic signal to the alternating current signal; and
determining, using a processor, a position of the magnetizing coil with respect to the one or more magnetic nanoparticles based on the comparison of the detected acoustic signal and the alternating current signal applied.

2. The method of claim 1, further comprising:
providing the one or more magnetic nanoparticles at the first location, the one or more magnetic nanoparticles comprising ferrite, ferrite alloy, mixtures of ferrite and non-metal material, nickel, platinum, magnetic polymers, and combinations thereof.

3. The method of claim 1, further comprising: providing the one or more magnetic nanoparticles at the first location, wherein the one or more magnetic nanoparticles are configured to include a resistance generating structure on at least a portion of a surface of each of the one or more magnetic nanoparticles, the resistance generating structure being effective to overcome a resistance at the first location that would prevent the one or more magnetic nanoparticles from generating the acoustic signal.

4. The method of claim 3, wherein the resistance generating structure is selected from at least one of sugar, gel matrix, and styrene polymer.

5. The method of claim 1, further comprising providing the one or more magnetic nanoparticles at the first location, wherein the one or more magnetic nanoparticles are configured to include a resistance decreasing structure on at least a portion of a surface of each of the one or more magnetic nanoparticles, the resistance decreasing structure being effective to reduce a resistance at the first location that would prevent the one or more magnetic nanoparticles from generating the acoustic signal.

6. The method of claim 1, further comprising providing the one or more magnetic nanoparticles at the first location, wherein a diameter of at least some of the one or more magnetic nanoparticles is from about 4 nm to about 100 nm.

7. The method of claim 1, wherein applying an alternating current signal to a magnetizing coil to excite an alternating magnetic field includes applying a frequency of the alternating current of about 50 Hz to about 5 MHz.

8. The method of claim 1, wherein the alternating magnetic field has a magnetic induction of about 2 mT to about 80 mT.

9. The method of claim 1, further comprising:
measuring a frequency of the alternating current signal;
measuring a frequency of the acoustic signal generated by the oscillating magnetic nanoparticles located in the first location; and
comparing the frequency of the alternating current signal and the frequency of the acoustic signal.

10. The method of claim 9, wherein comparing the frequency of the alternating current signal and the frequency of the acoustic signal further comprises determining a correct position of the magnetizing coil based on the comparison of the frequency of the alternating current and the frequency of the acoustic signal.

11. The method of claim 10, further comprising repositioning the magnetizing coil based on the comparison of the frequency of the alternating current signal and the frequency of the acoustic signal.

12. An apparatus comprising:
a magnetizing coil;
a current driver amplifier coupled to the magnetizing coil;
a direct digital synthesizer coupled to the current driver amplifier, that when in operation, operates with the current driver amplifier to supply an alternating current to the magnetizing coil to generate an alternating magnetic field in the magnetizing coil near one or more magnetic nanoparticles;
an acoustic probe configured to receive an acoustic signal;
a preamplifier coupled to the acoustic probe, that when in operation, operates with the preamplifier and acoustic probe to measure a frequency of the acoustic signal generated by the alternating magnetic field; and
a double frequency synchronous cross-detector coupled to the preamplifier and coupled to the direct digital synthesizer,
wherein, during operation, the direct digital synthesizer sends a measurement of the alternating current signal to the double frequency synchronous cross-detector; and
wherein, during operation, the double frequency synchronous cross-detector compares the measurement of the frequency of the acoustic signal and the measurement of the alternating current signal, and detects a doubled acoustic frequency of the acoustic signal that is approximately twice a frequency of the alternating current signal, which is indicative of a correct position of the magnetizing coil.

13. The apparatus of claim 12, further comprising a graphical user interface for displaying the approximately doubled acoustic frequency of the acoustic signal in the form of a visual output.

14. A system for a medical treatment comprising:
a magnetizing coil configured to be placed near a first location having a plurality of magnetic nanoparticles;
an alternating current generator coupled to the magnetizing coil and configured to generate an alternating magnetic field in the magnetizing coil, responsive to an applied alternating current signal, effective for oscillating the plurality of magnetic nanoparticles;
an acoustic probe configured to be placed near the first location having the plurality of magnetic nanoparticles;
a first detector communicating with the alternating current generator for generating a first measurement of an alternating magnetic field generated in the magnetizing coil;
a second detector communicating with the acoustic probe for generating a second measurement of an acoustic signal generated by the plurality of nanoparticles oscillating at the first location by the magnetic field; and
a double frequency synchronous cross-detector coupled to the first detector and the second detector,
wherein, during operation, the double frequency synchronous cross-detector compares the applied alternating current signal and the acoustic signal, and detects a doubled acoustic frequency of the acoustic signal that is approximately twice a frequency of the alternating current signal, which is indicative of a position of the magnetizing coil with respect to the plurality of magnetic nanoparticles.

15. The system of claim 14, further comprising a processor generating an output of a determination of a positioning of the magnetic coil with respect to the magnetic nanoparticles based on the approximately doubled acoustic frequency.

16. The system of claim 15, further comprising a graphical user interface communicating with the processor to graphically display the output generated by the processor.

17. The system of claim 14 further comprising a computing device communicating with the first detector and the second detector, wherein the computing device comprises, one or more of a desktop computer, workstation computer, a computing system comprised of a cluster of processors, a networked computer, a tablet personal computer, a laptop computer, or a personal digital assistant.

18. A method for a medical treatment comprising:
  applying an alternating current signal to a magnetizing coil in order to excite an alternating magnetic field near one or more magnetic nanoparticles at a first location, the alternating magnetic field effective to increase an oscillation of the one or more magnetic nanoparticles at the first location and generate an acoustic signal;
  detecting the alternating magnetic field excited with a first detector;
  detecting the acoustic signal with a second detector;
  comparing the detected acoustic signal to the alternating magnetic field; and
  determining, using a processor, a position of the magnetizing coil with respect to the one or more magnetic nanoparticles based on the comparison of the detected acoustic signal and the alternating magnetic field detected.

* * * * *

UNITED STATES PATENT AND TRADEMARK OFFICE
CERTIFICATE OF CORRECTION

Page 1 of 1

PATENT NO. : 8,251,885 B2
APPLICATION NO. : 12/564695
DATED : August 28, 2012
INVENTOR(S) : Ueda et al.

It is certified that error appears in the above-identified patent and that said Letters Patent is hereby corrected as shown below:

In Column 3, Line 61, delete "Carboxi dextran." and insert -- Carboxydextran. --, therefor.

In Column 15, Line 53, delete "atherothromobosis" and insert -- atherothrombosis --, therefor.

In Column 20, Line 57, delete "Direct Digital Synthesizer" and insert -- Direct Digital Synthesizer (DDS): --, therefor.

In Column 20, Line 59, delete "convertor" and insert -- converter --, therefor.

In Column 20, Line 61, delete "500 Hz" and insert -- 500 Hz. --, therefor.

In Column 20, Line 64, delete "300 mA" and insert -- 300 mA. --, therefor.

In Column 20, Line 67, delete "sensor" and insert -- sensor. --, therefor.

Signed and Sealed this
First Day of January, 2013

David J. Kappos
*Director of the United States Patent and Trademark Office*